US011983156B2

(12) United States Patent
Alford

(10) Patent No.: US 11,983,156 B2
(45) Date of Patent: May 14, 2024

(54) SYSTEM AND METHOD FOR INDEXING LARGE VOLUMES AND DURATIONS OF TEMPORALLY-BASED SENSOR DATASETS

(71) Applicant: Janak Babaji Alford, Ottawa (CA)

(72) Inventor: Janak Babaji Alford, Ottawa (CA)

(*) Notice: Subject to any disclaimer, the term of this patent is extended or adjusted under 35 U.S.C. 154(b) by 0 days.

(21) Appl. No.: 17/888,728

(22) Filed: Aug. 16, 2022

(65) Prior Publication Data

US 2023/0059697 A1    Feb. 23, 2023

Related U.S. Application Data

(60) Provisional application No. 63/233,998, filed on Aug. 17, 2021.

(51) Int. Cl.

| | | |
|---|---|---|
| *G06F 7/00* | (2006.01) |
| *A61B 5/16* | (2006.01) |
| *G06F 16/22* | (2019.01) |
| *G06F 16/28* | (2019.01) |
| *G06N 3/006* | (2023.01) |
| *G06N 3/045* | (2023.01) |
| *G06N 3/094* | (2023.01) |
| *G06T 13/40* | (2011.01) |
| *G06V 10/764* | (2022.01) |
| *G06V 40/16* | (2022.01) |
| *G06V 40/20* | (2022.01) |
| *G10L 25/63* | (2013.01) |

(52) U.S. Cl.
CPC ......... *G06F 16/2219* (2019.01); *A61B 5/167* (2013.01); *G06F 16/287* (2019.01); *G06N 3/006* (2013.01); *G06N 3/045* (2023.01); *G06N 3/094* (2023.01); *G06T 13/40* (2013.01); *G06V 10/764* (2022.01); *G06V 40/174* (2022.01); *G06V 40/20* (2022.01); *G10L 25/63* (2013.01)

(58) Field of Classification Search
CPC ............... G06F 16/2219; G06F 16/287; G06F 16/2477; G06F 16/285; G06V 40/174; G06V 40/20; G06V 10/764; G06N 3/094; G06N 3/045; G06N 3/006; G06N 3/08; A61B 5/167; G06T 13/40; G10L 25/63
USPC ....... 707/722, 736, 737, 740, 692, 741, 752, 707/783

See application file for complete search history.

(56) References Cited

U.S. PATENT DOCUMENTS

| | | | | |
|---|---|---|---|---|
| 2012/0197856 A1* | 8/2012 | Banka | ................. | H04L 67/2885 707/706 |
| 2018/0284758 A1* | 10/2018 | Cella | .................. | G05B 23/0291 |

* cited by examiner

*Primary Examiner* — Md I Uddin
(74) *Attorney, Agent, or Firm* — White-Welker & Welker, LLC; Matthew T. Welker, Esq.

(57) ABSTRACT

A system and method to index one or more sensor-based datasets utilizing pattern recognition and prediction to identify instances and regions of novelty and change as a means of highlighting potential subjective interest for the purposes of optimizing the manual and automated search, visualization, and extraction of datasets.

18 Claims, 23 Drawing Sheets

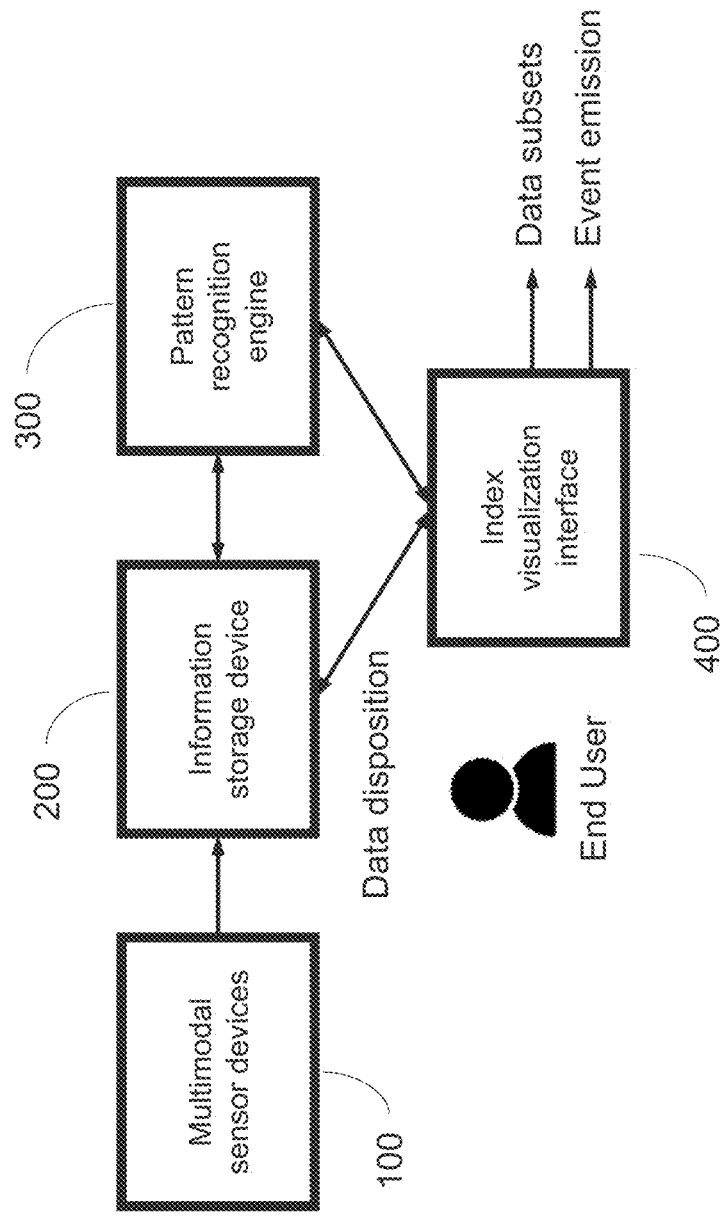
Fig 1. Overall composition of the invention

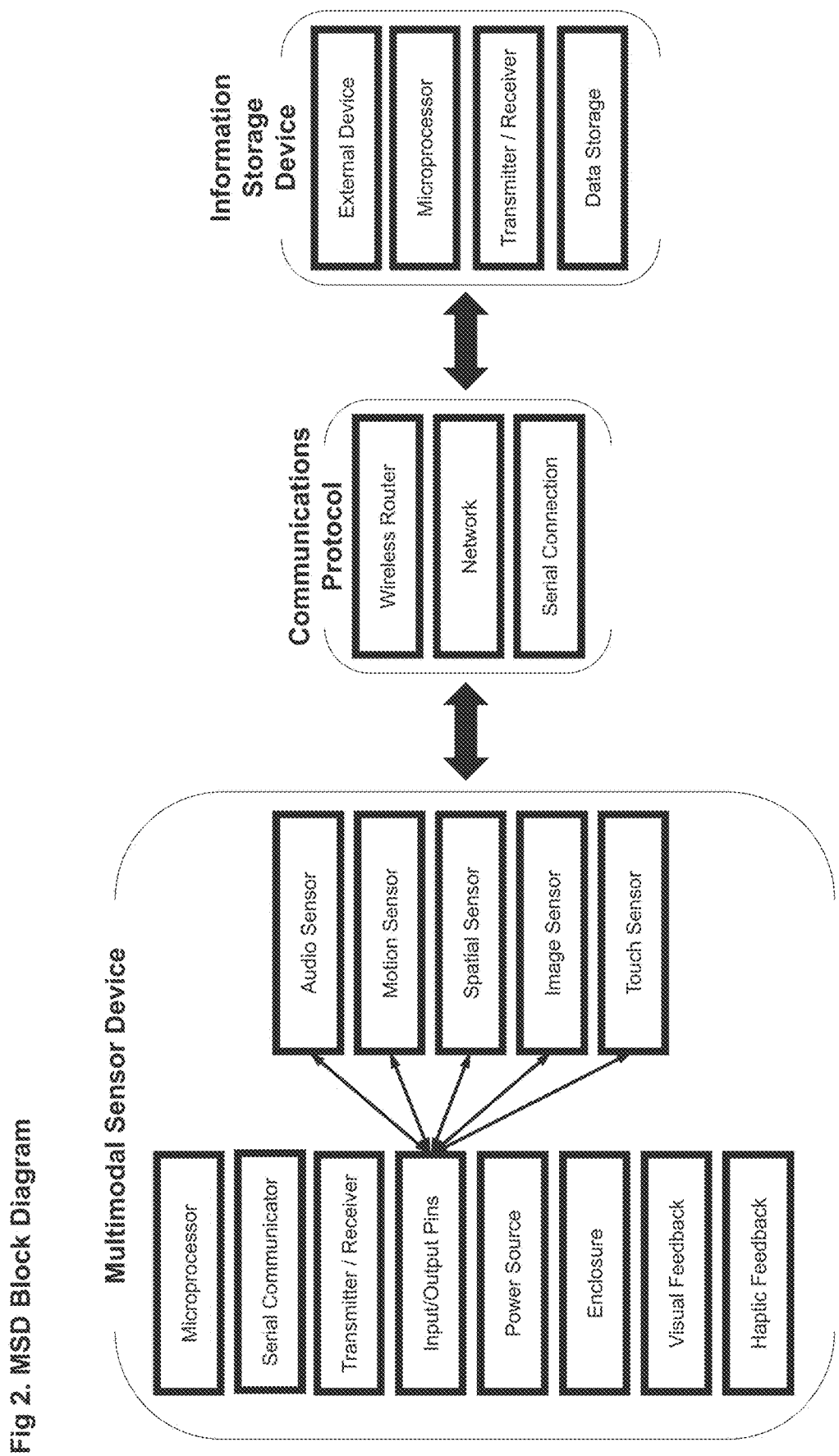
Fig 2. MSD Block Diagram

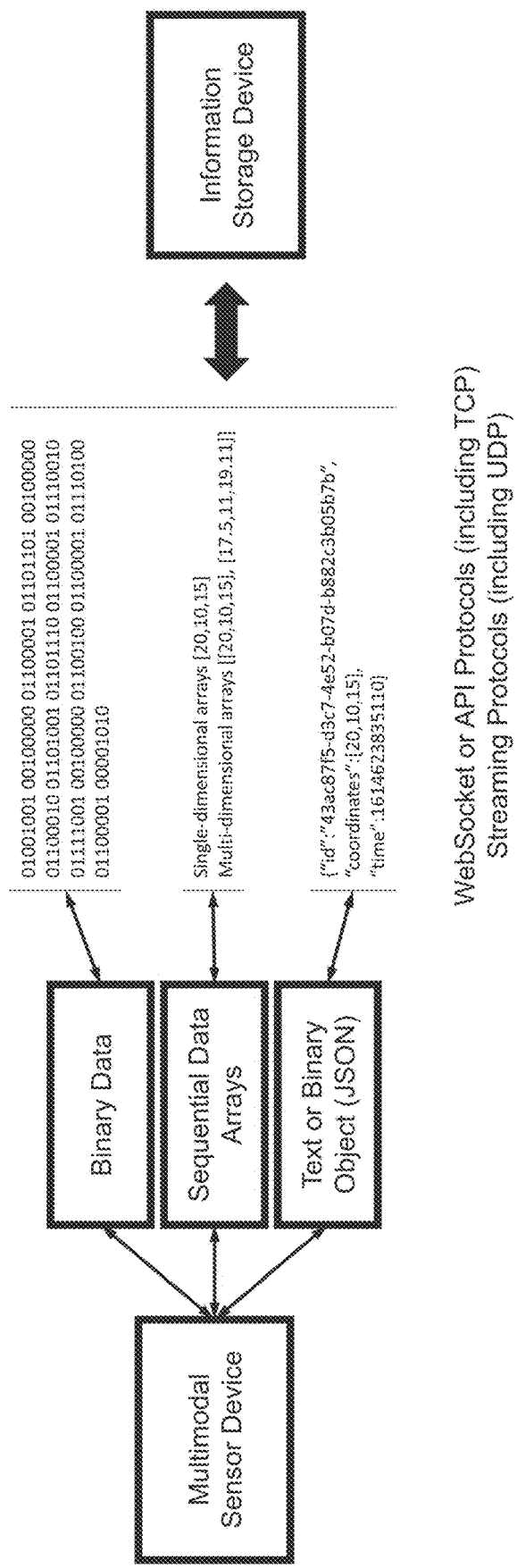

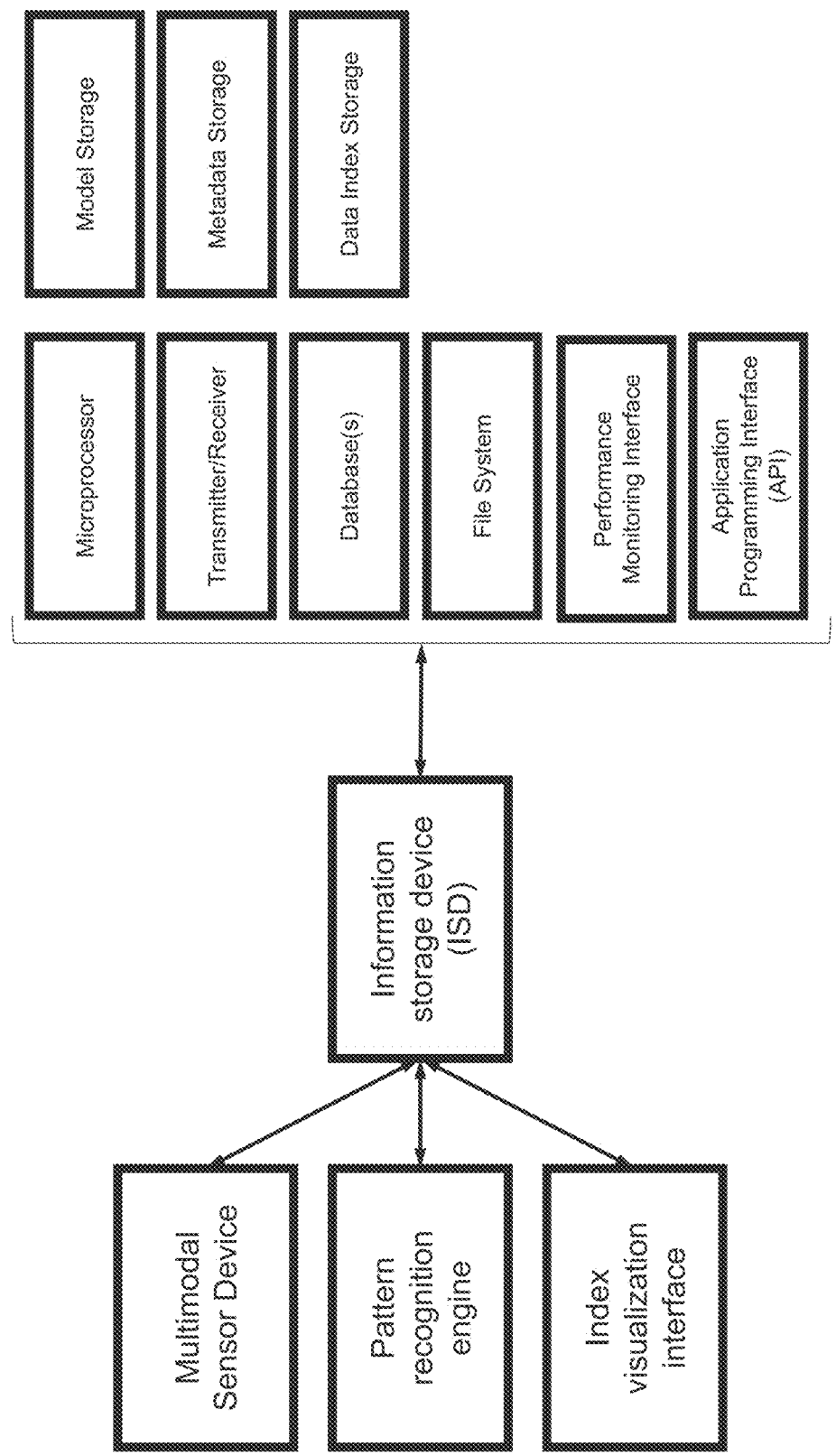
Fig 4. ISD Block Diagram

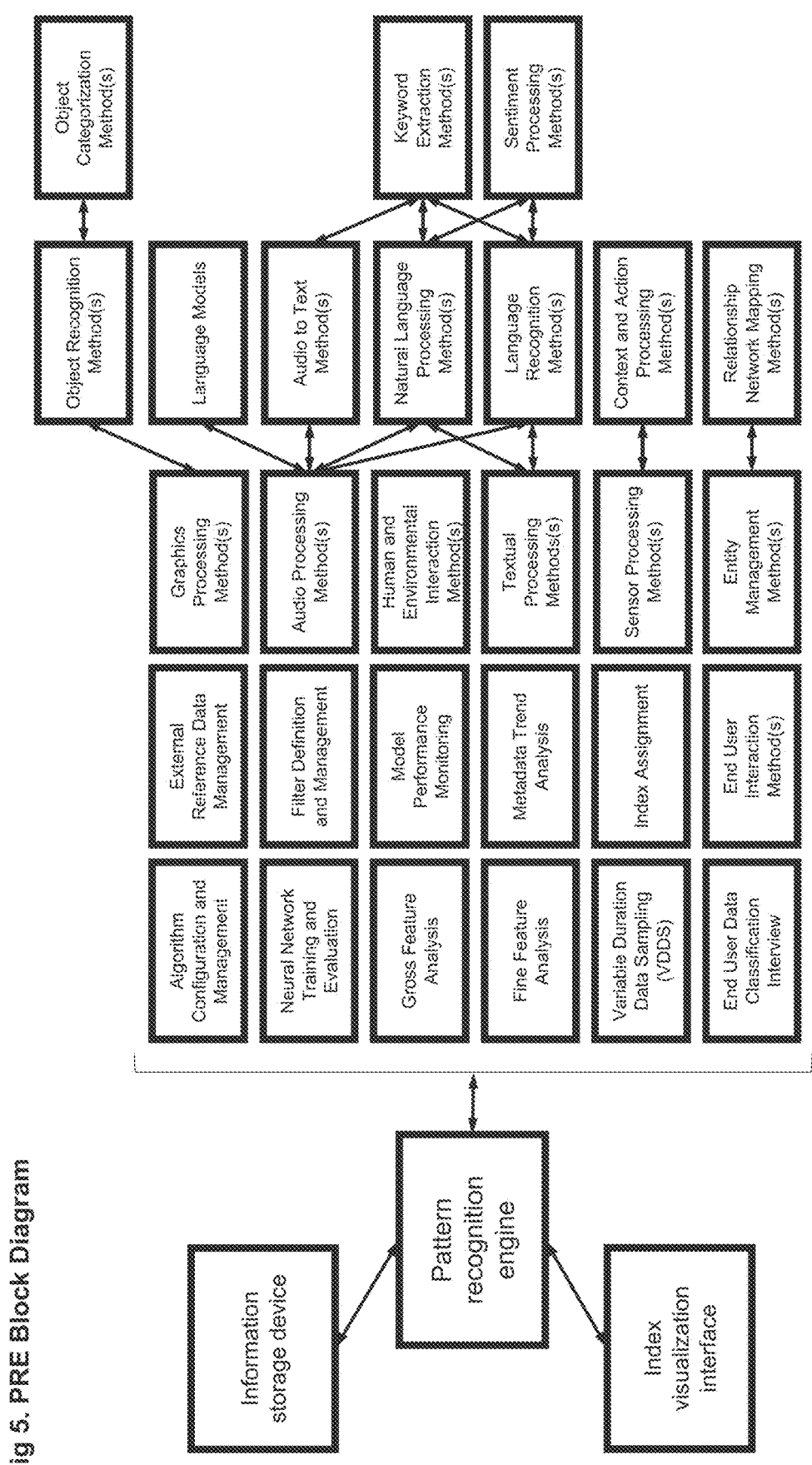
Fig 5. PRE Block Diagram

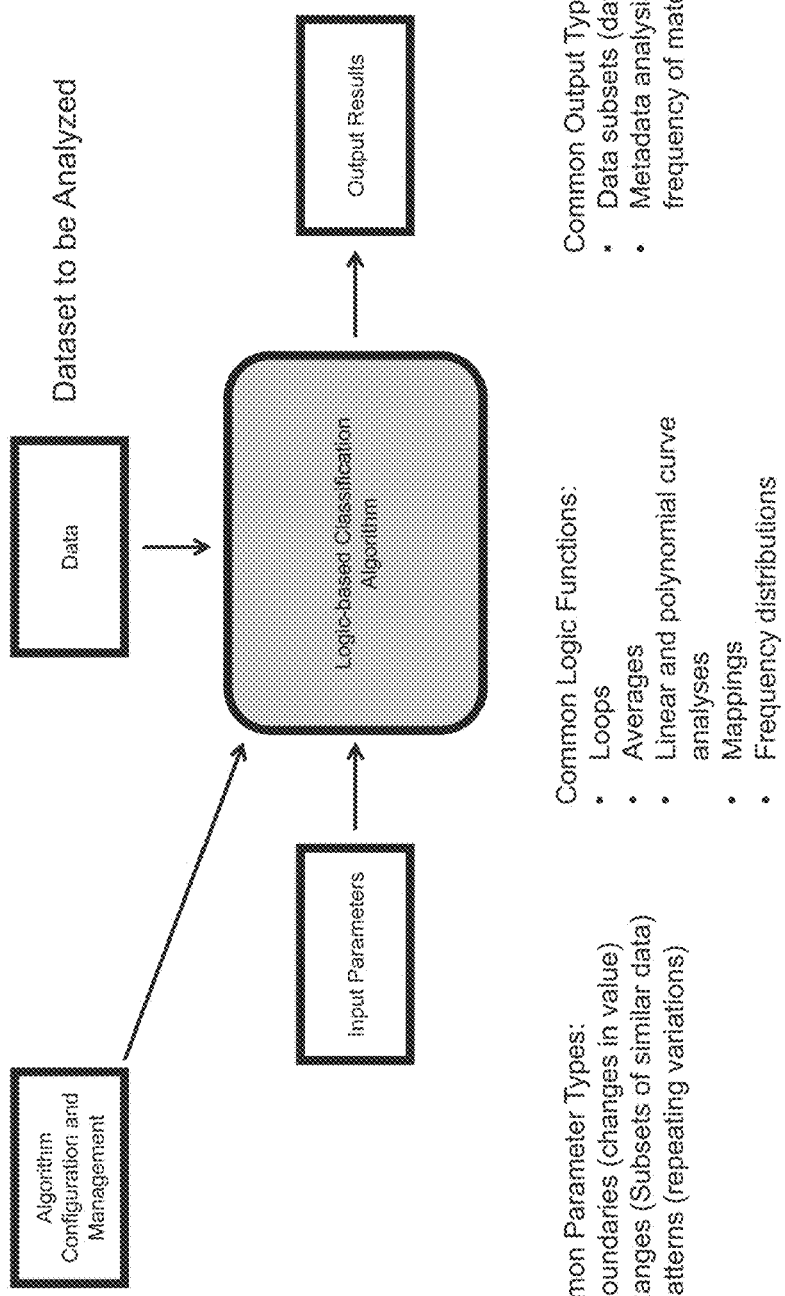

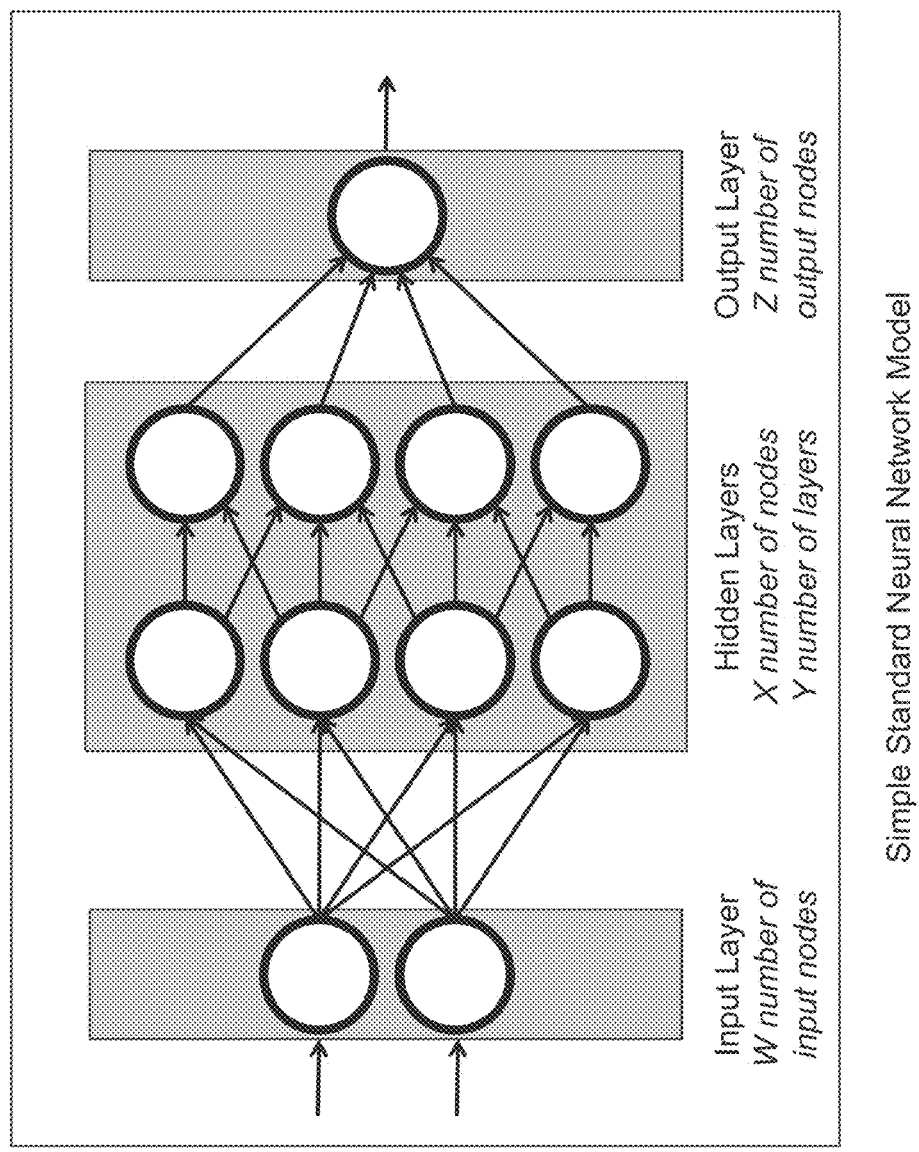
Fig 7. PRE Neural Network Definition

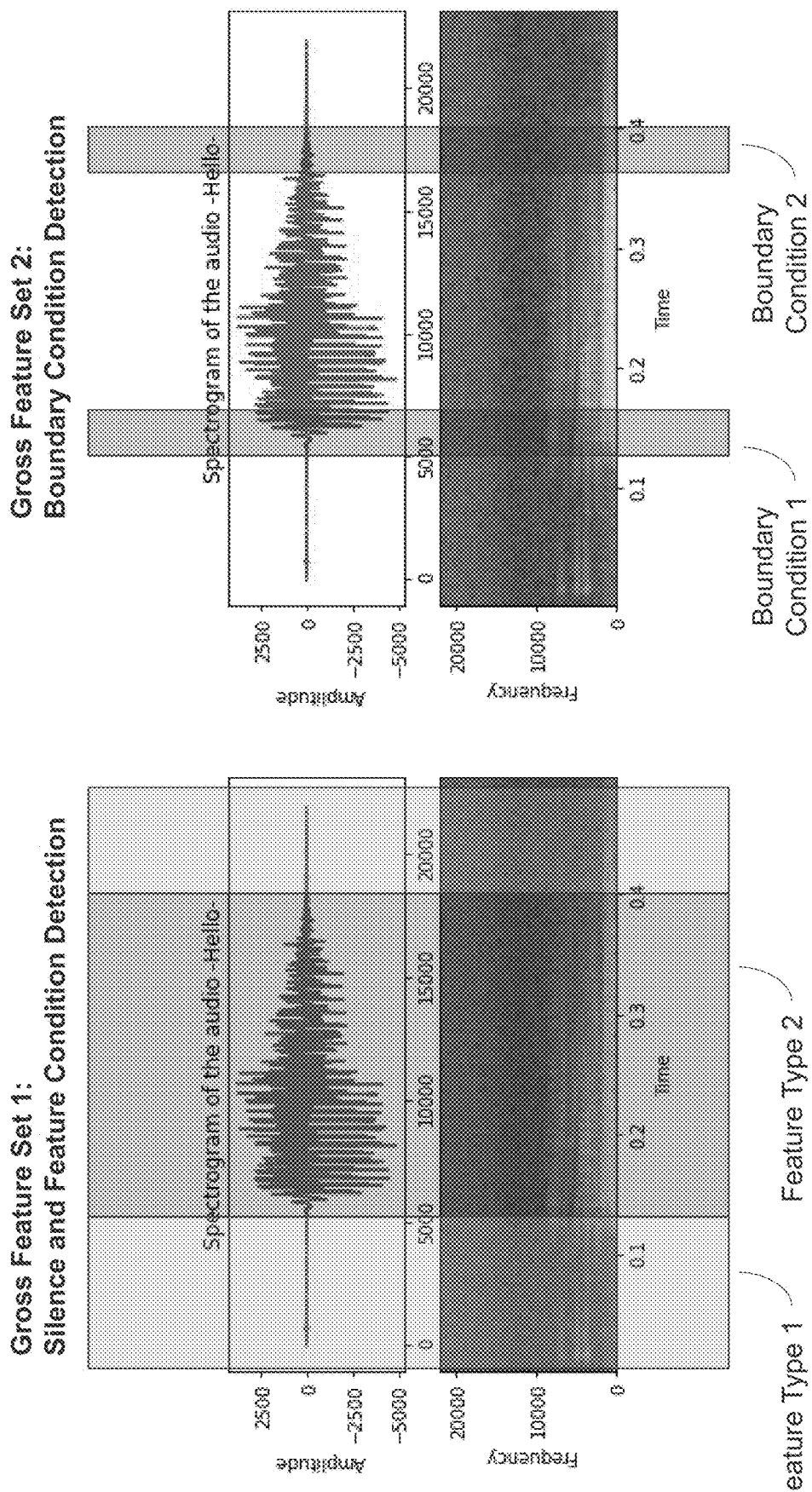

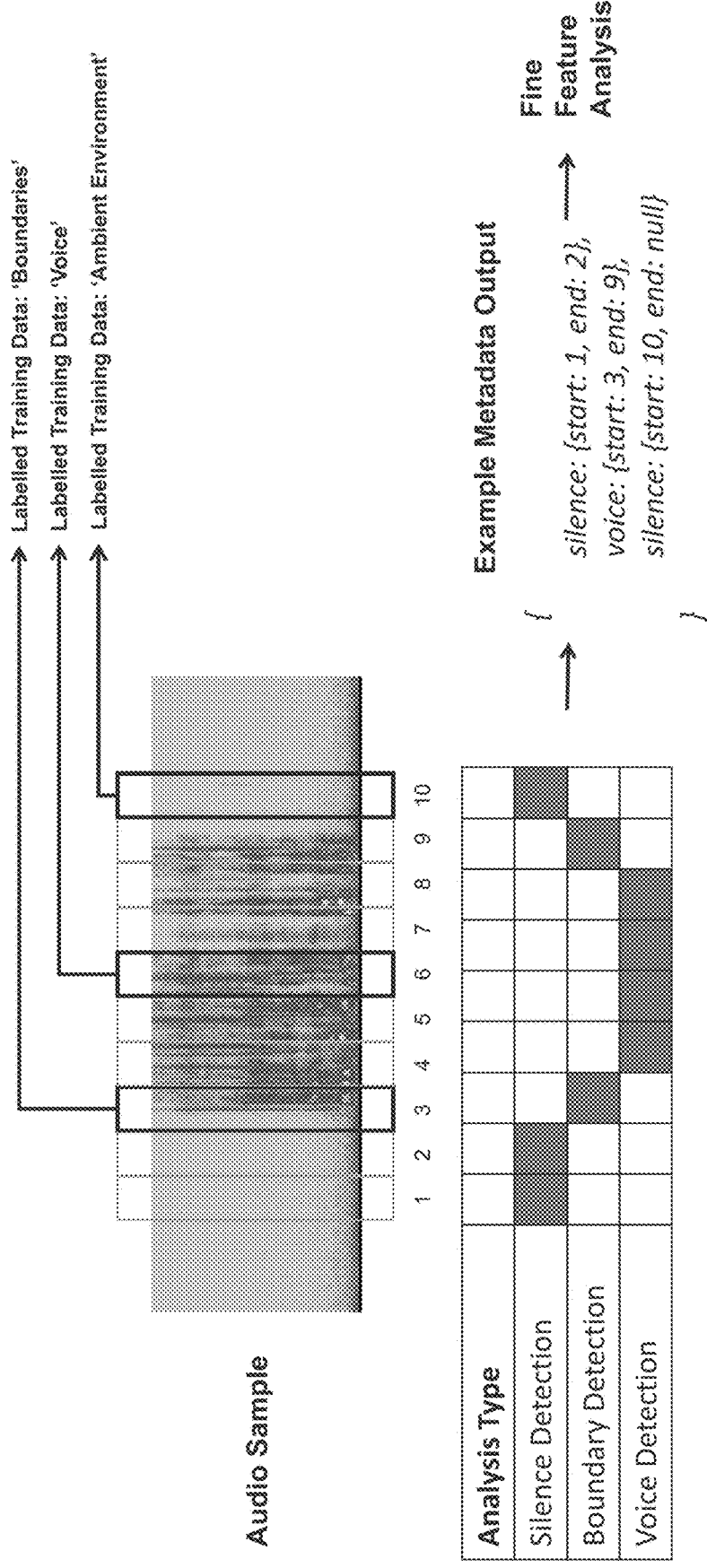

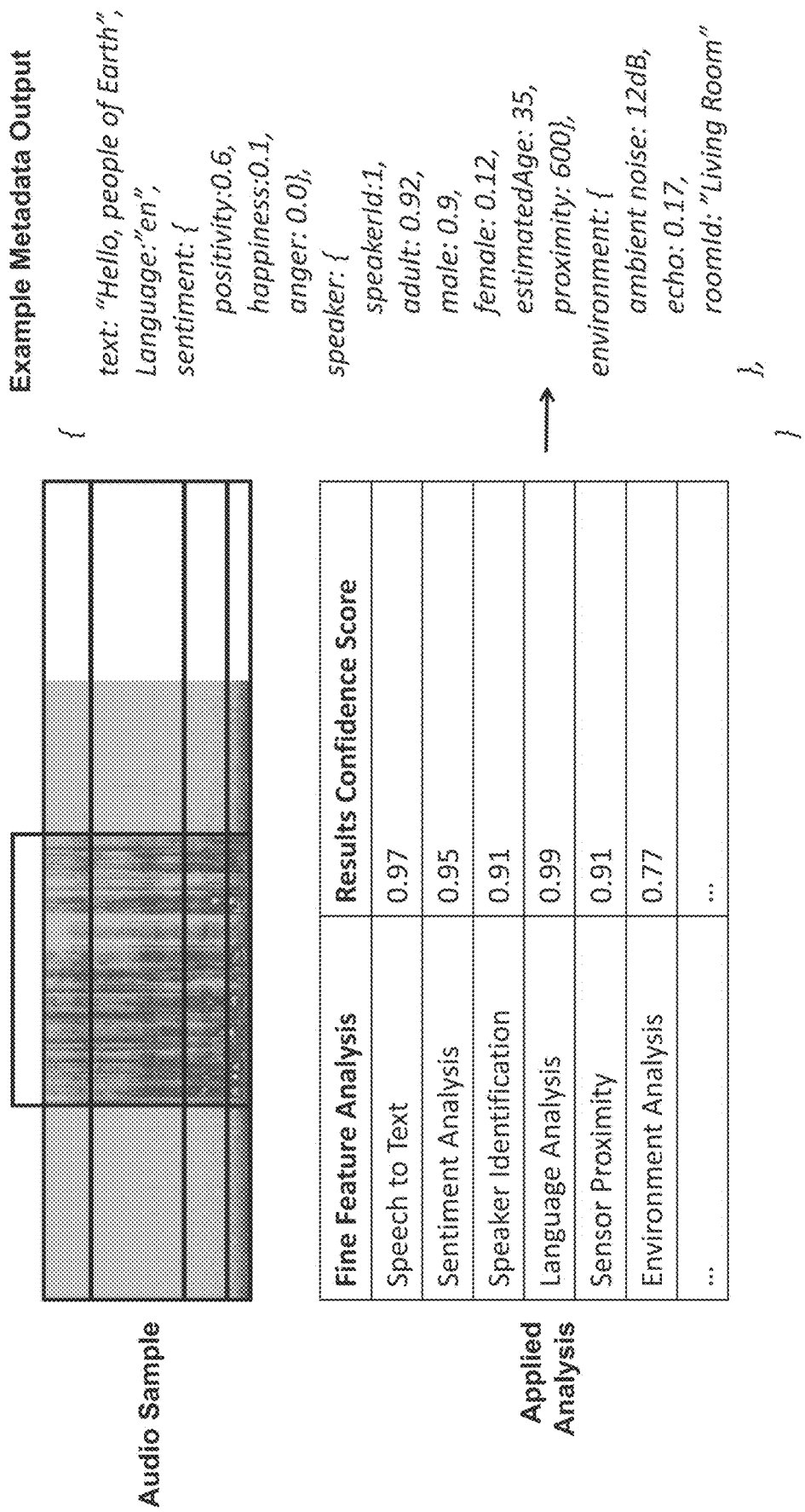

Fig 11. PRE Fine Feature Analysis (Image Example)

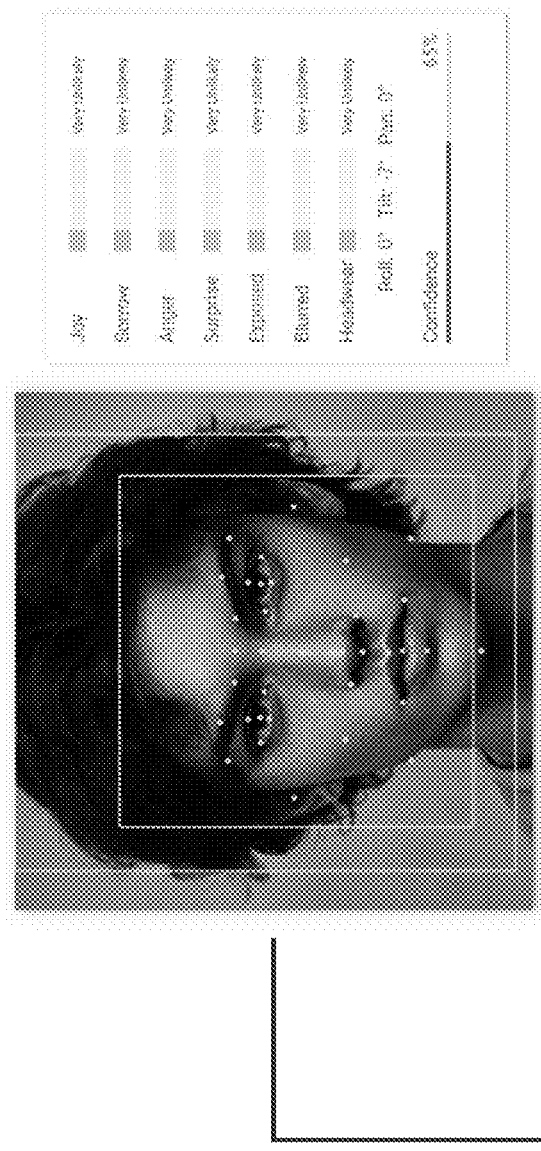

Example End User Characteristics

```
{
  "attributes": {
    "age": 28,
    "asian": 0.52738,
    "black": 0.40954,
    "gender": {
      "femaleConfidence": 0,
      "maleConfidence": 1,
      "type": "M"
    },
    "glasses": "None",
    "hispanic": 0.02168,
    "lips": "Together",
    "other": 0.0277,
    "white": 0.0137
  },
  "eyeDistance": 528,
  "face_id": 1,
}
```

Example Facial Features Classification

5oclock shadow: yes (11%), black hair: yes (65%), glasses: no, pale skin: no (23%), wearing earrings: no (46%),
age: 22 (60%), blond hair: no, goatee: no (61%), pitch: -10.19, wearing hat: no (39%),
arched eyebrows: no (4%), blurry: no, gray hair: no, pointy nose: no (17%), wearing lipstick: no (60%),
attractive: yes (27%), brown hair: no (87%), heavy makeup: no (68%), race: asian (91%), wearing necklace: no (59%),
bags under eyes: yes (18%), bushy eyebrows: yes, high cheekbones: no (84%), receding hairline: no (84%), wearing necktie: no (57%),
bald: no, chubby: no (95%), mouth open: no (97%), rosy cheeks: no, yaw: 2.38,
beard: no (28%), double chin: no, mustache: no (55%), sideburns: no (62%), young: yes,
big lips: yes (13%), expression: neutral, narrow eyes: no (47%), straight hair: no (31%),
big nose: yes (17%), gender: male (45%), oval face: no (2%), wavy hair: no (3%), Fig 12. PRE Multiple Characteristic Extraction and Occurrence Measurement Audio data may contain dozens of characteristics, each which through extraction can be used to train a unique neural network.

Occurrence of these characteristics (frequency, volume, amplitude) within the metadata create patterns which can be mapped over time through metadata analysis.

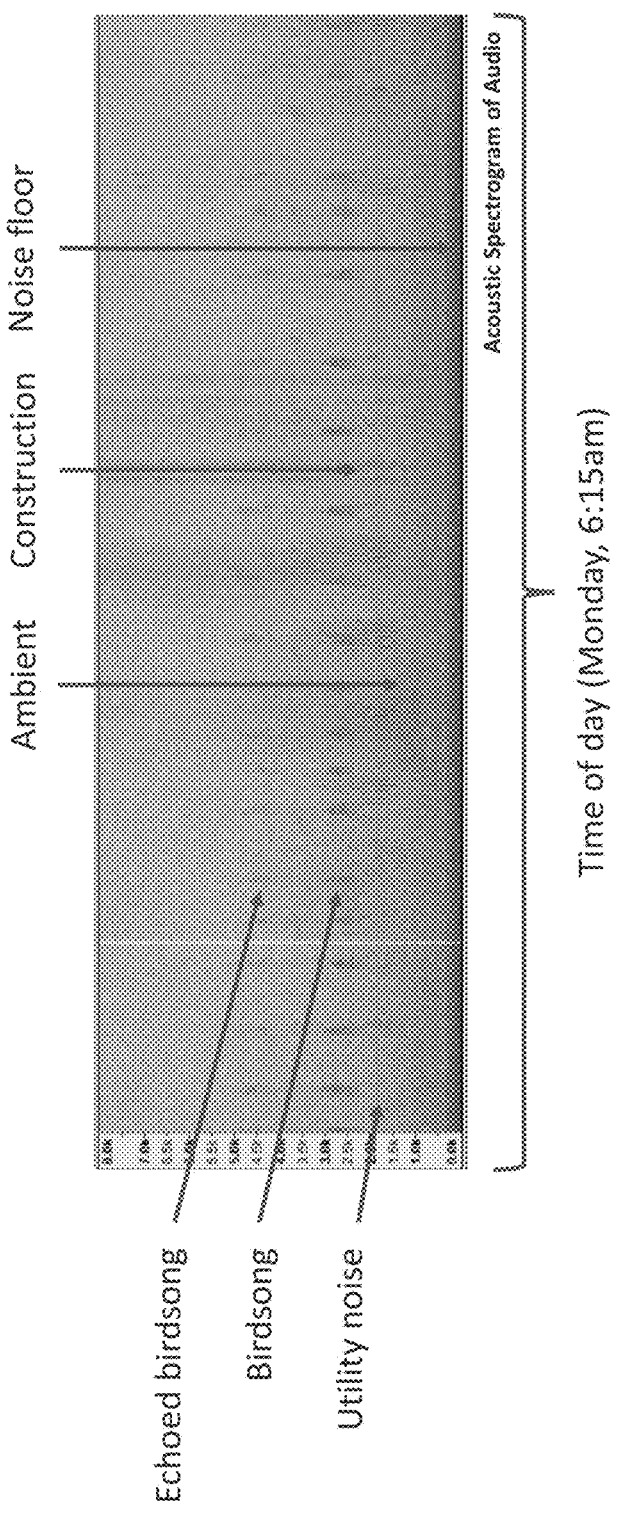

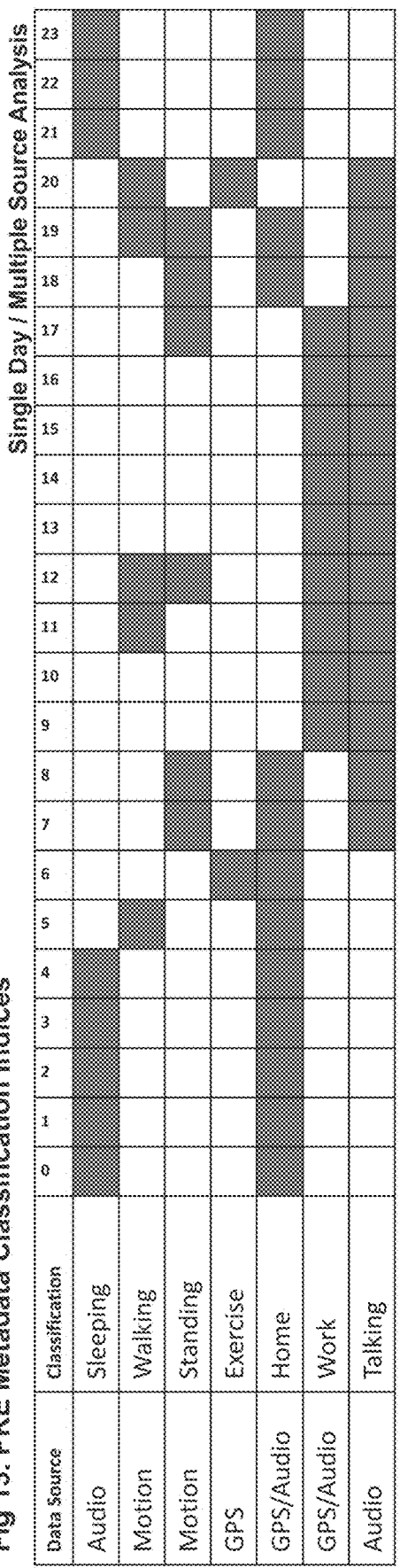
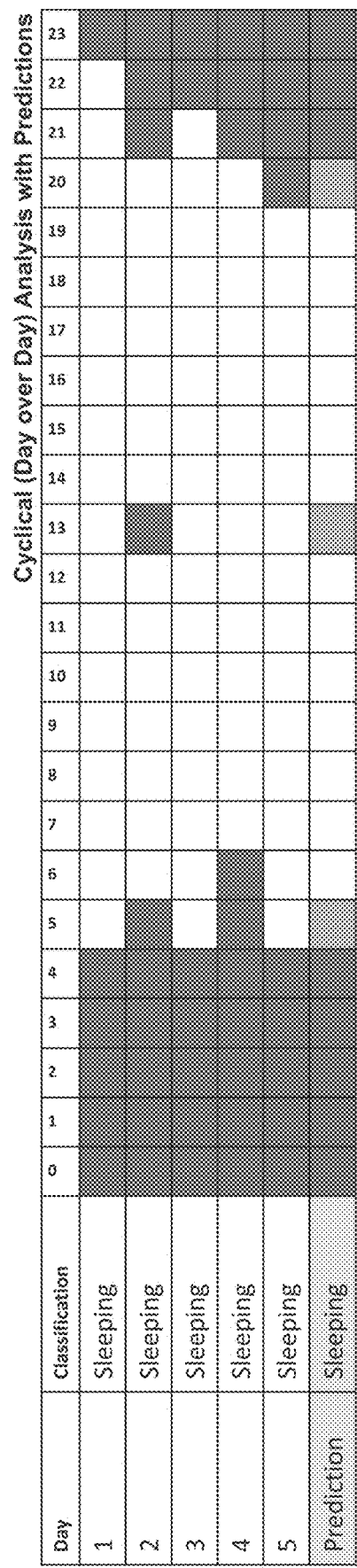
Fig 13. PRE Metadata Classification Indices

Fig 14. PRE Metadata Narrative Indices
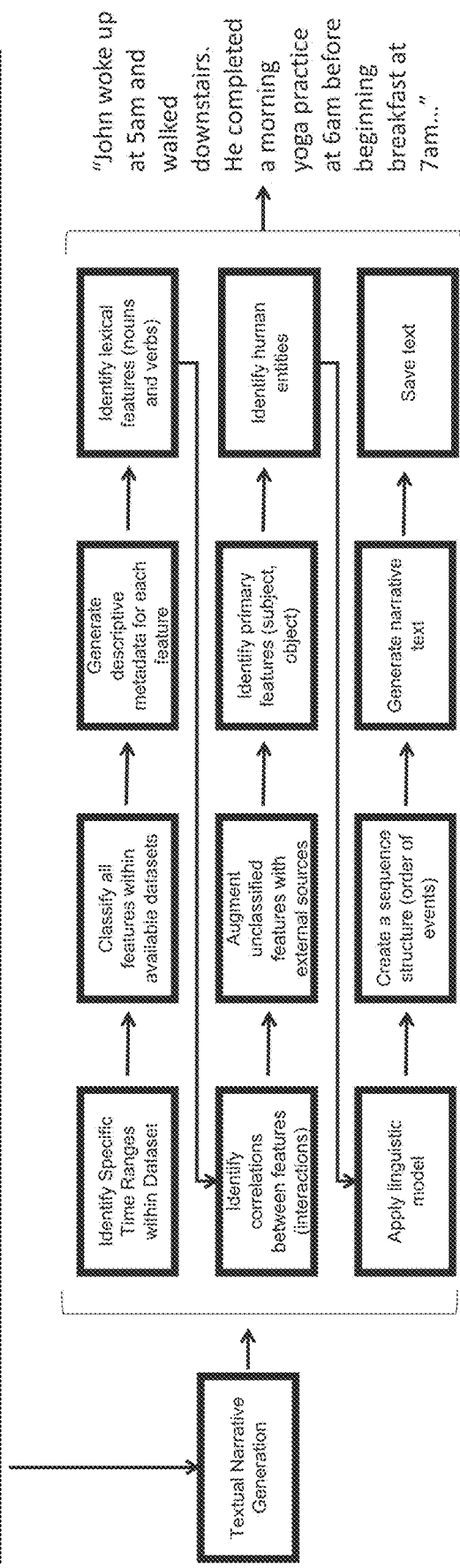

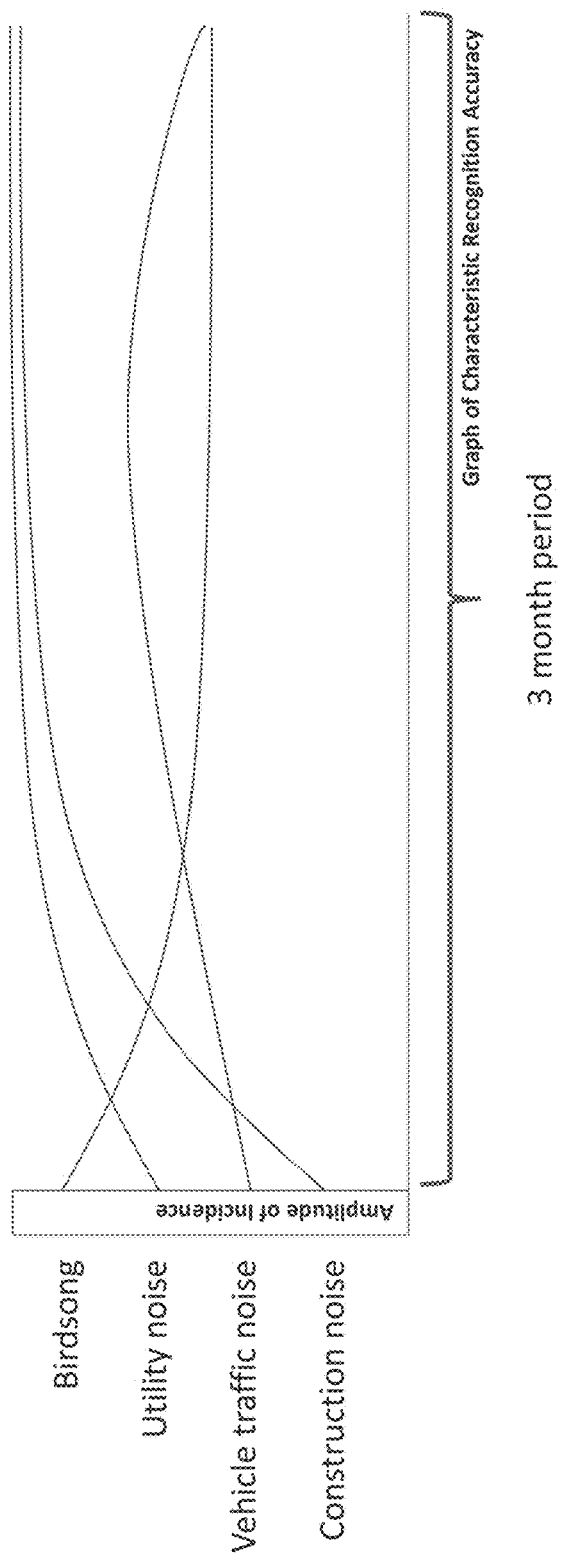

Fig 15. PRE Model Visualization of Characteristic Occurrence Identification Over Time Characteristic presence may apply multiple measurement criteria including:
- Monitoring the presence of previously mapped characteristics and recording their amplitude of incidence;
- Monitoring the accuracy of each model's ability to accurately recognize characteristics

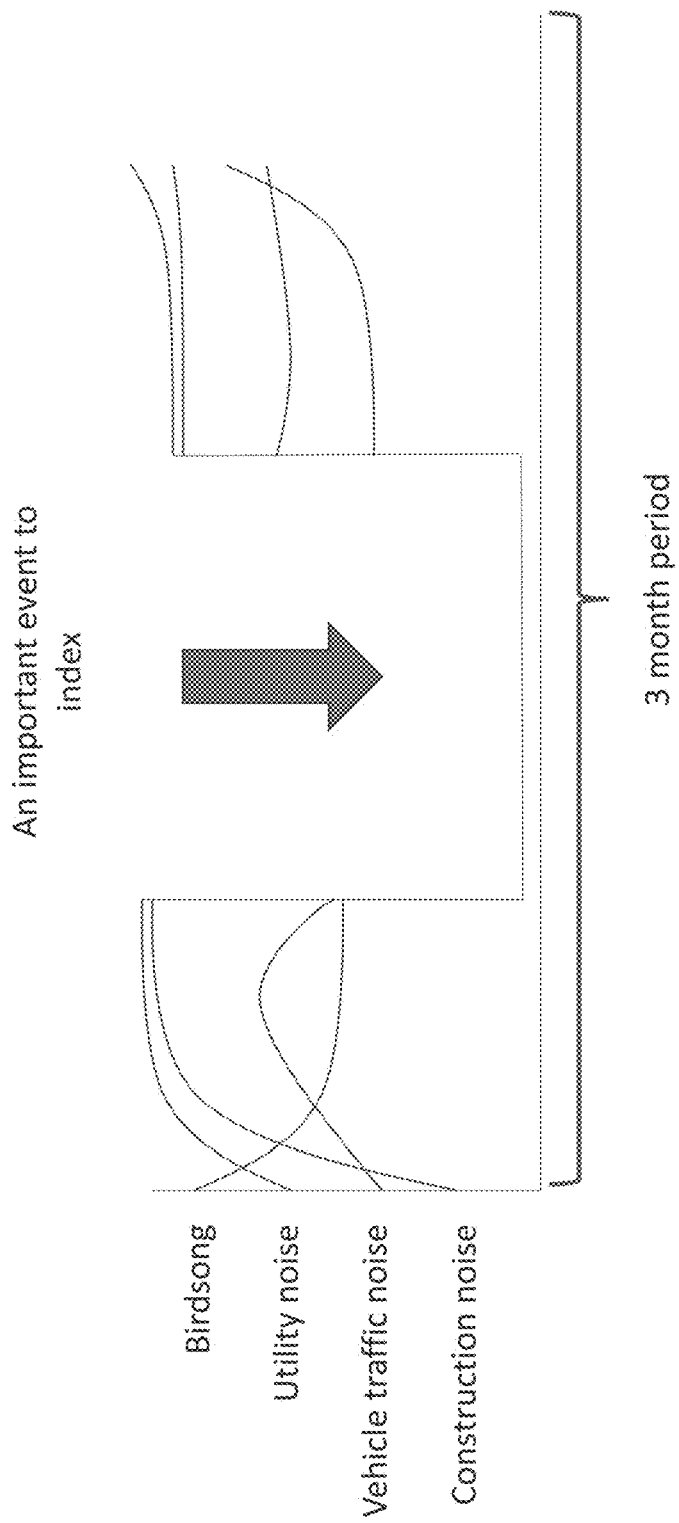
Fig 16. PRE Multi-Model Consensus Divergence

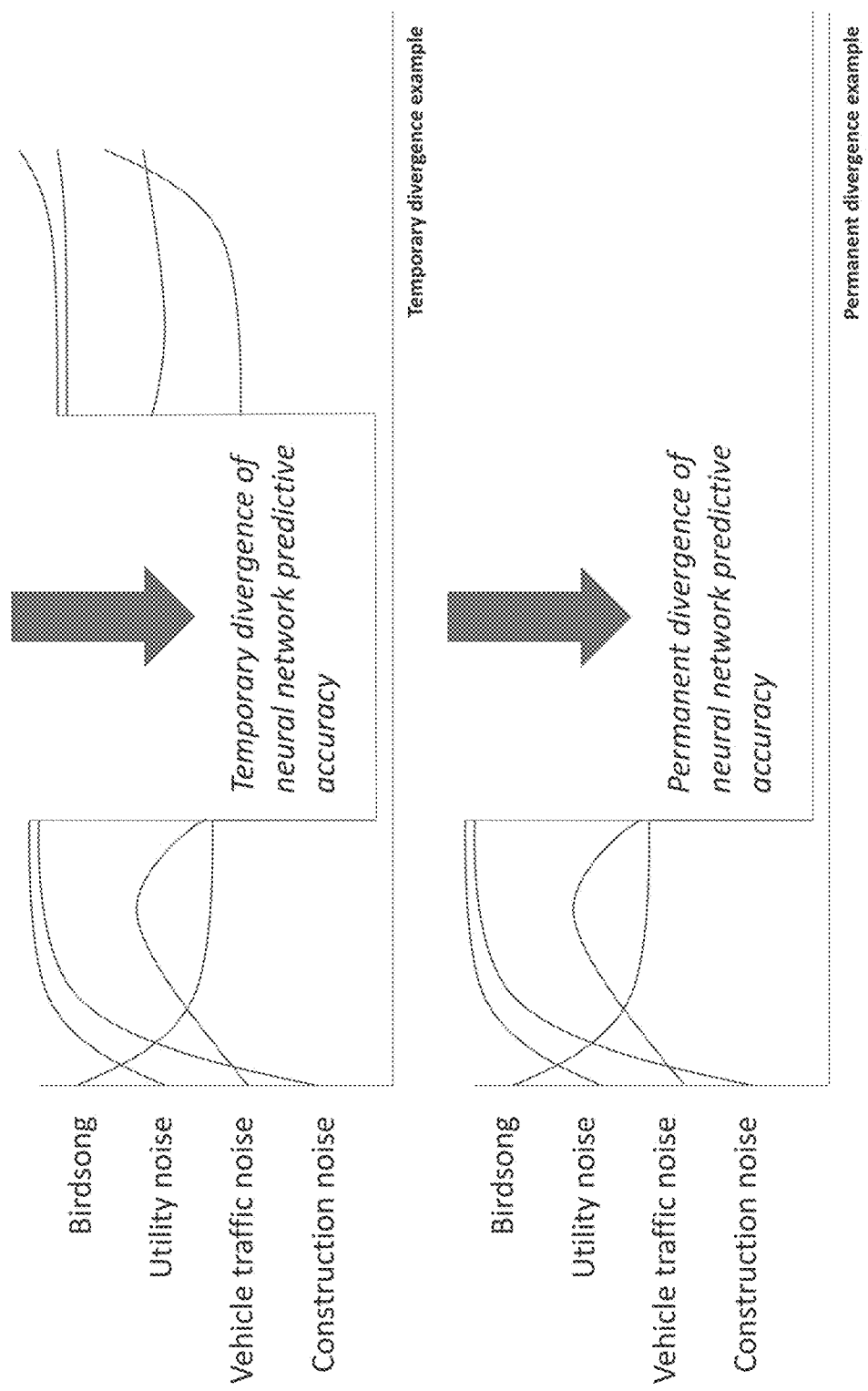
Fig 17. PRE Model Temporary Divergence vs. Permanent Divergence

Fig 18. PRE Model Performance Peaks and Plateaus

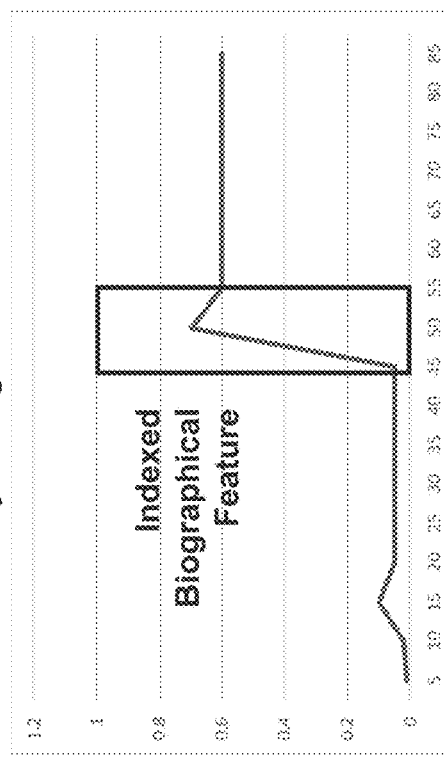

Model Accuracy Divergence "Plateau"

Permanent life event changed the classification quality of a trained neural network model. The classification quality of the model never returned.

Analysis: A permanent change in the end user's habits. A new model must be developed.

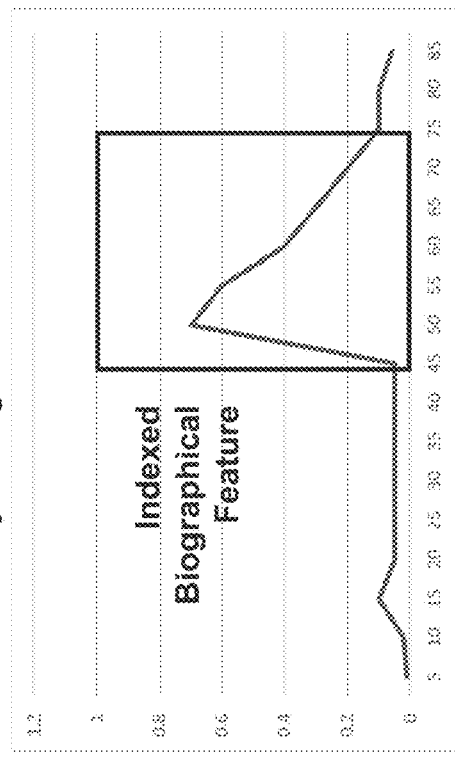

Model Accuracy Divergence "Peak"

Temporary life event changed the classification quality of a trained neural network model. Over time, without retraining model, the classification quality increased as the end user's actions re-aligned to training data.

Analysis: A temporary change in the end user's habits and patterns.

Fig 19. PRE Models Divergence Over a Lifetime

- Viewed over a human lifetime, these divergences provide a visual index of eras of significant change.

- As context changes, old neural network models cease to function and new neural networks require data acquisition to learn the new environment. These periods of transition and the valleys between the peaks provide insight into the areas of heightened subjective interest.

- Applied toward indexing large datasets, model 'failure' through accuracy divergence provides a means of data indexing to support retrieval and interaction.

- Concurrent divergence (multiple factors changing / degree of change) provides greater insight into the degree of human interest into the data.

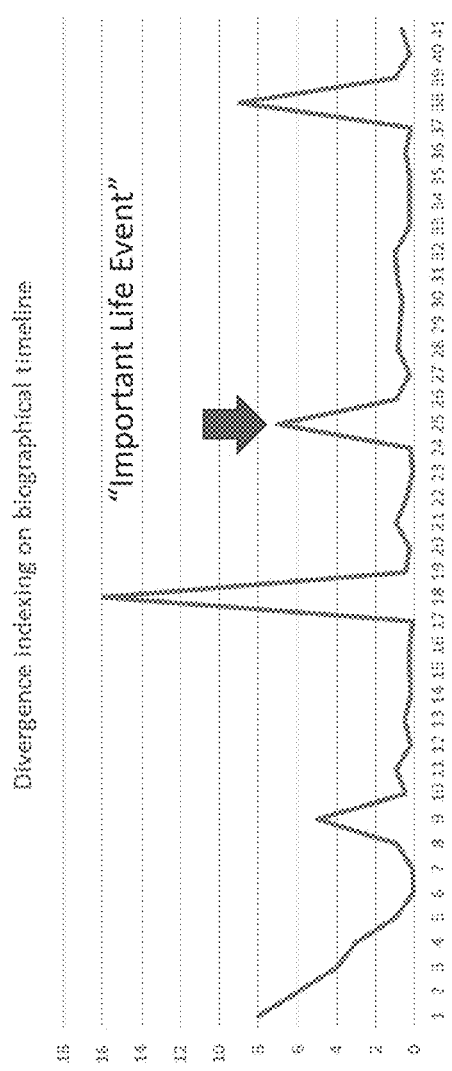

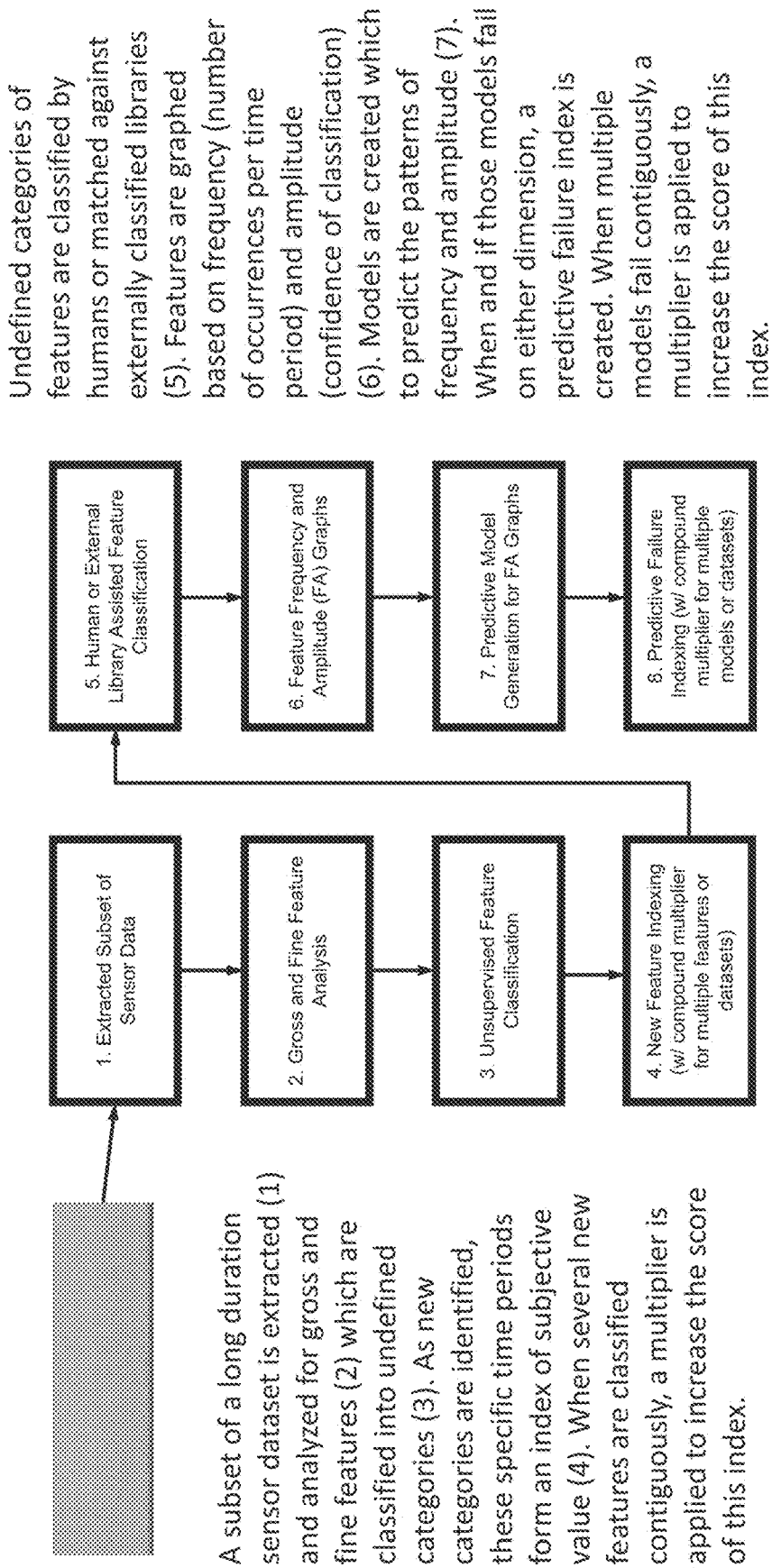
Fig 20. Layered Analysis Process

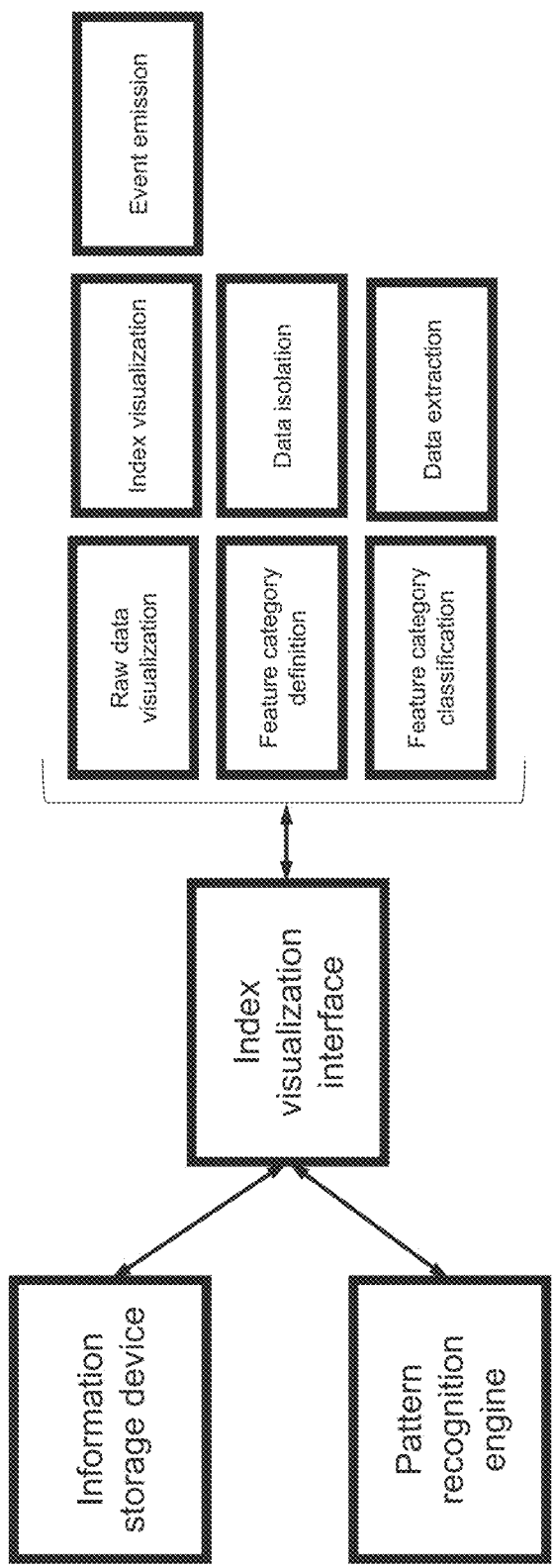
Fig 21. IVI Block Diagram

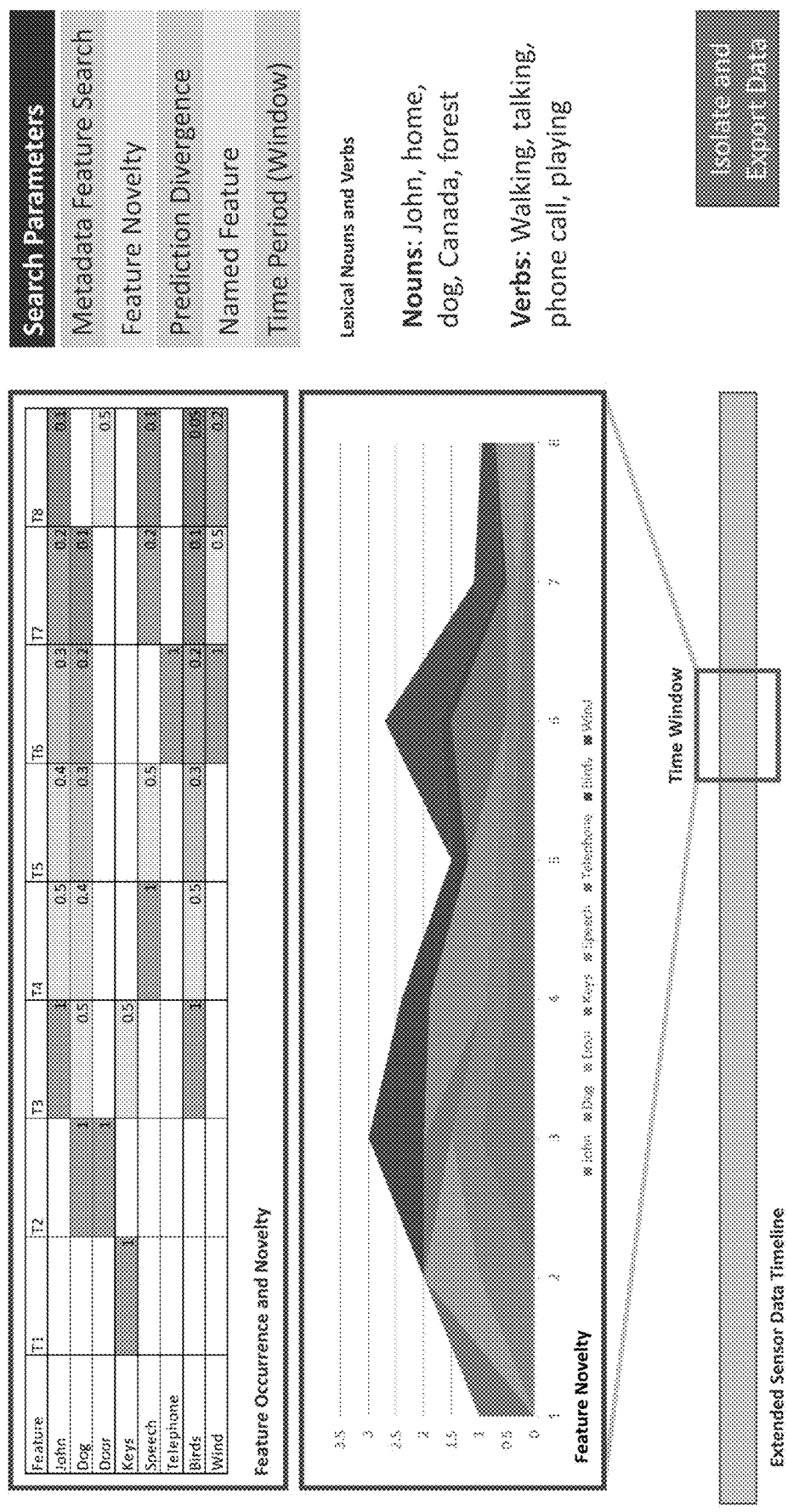
Fig 22. Example Index Visualization and Search Interface (Features)

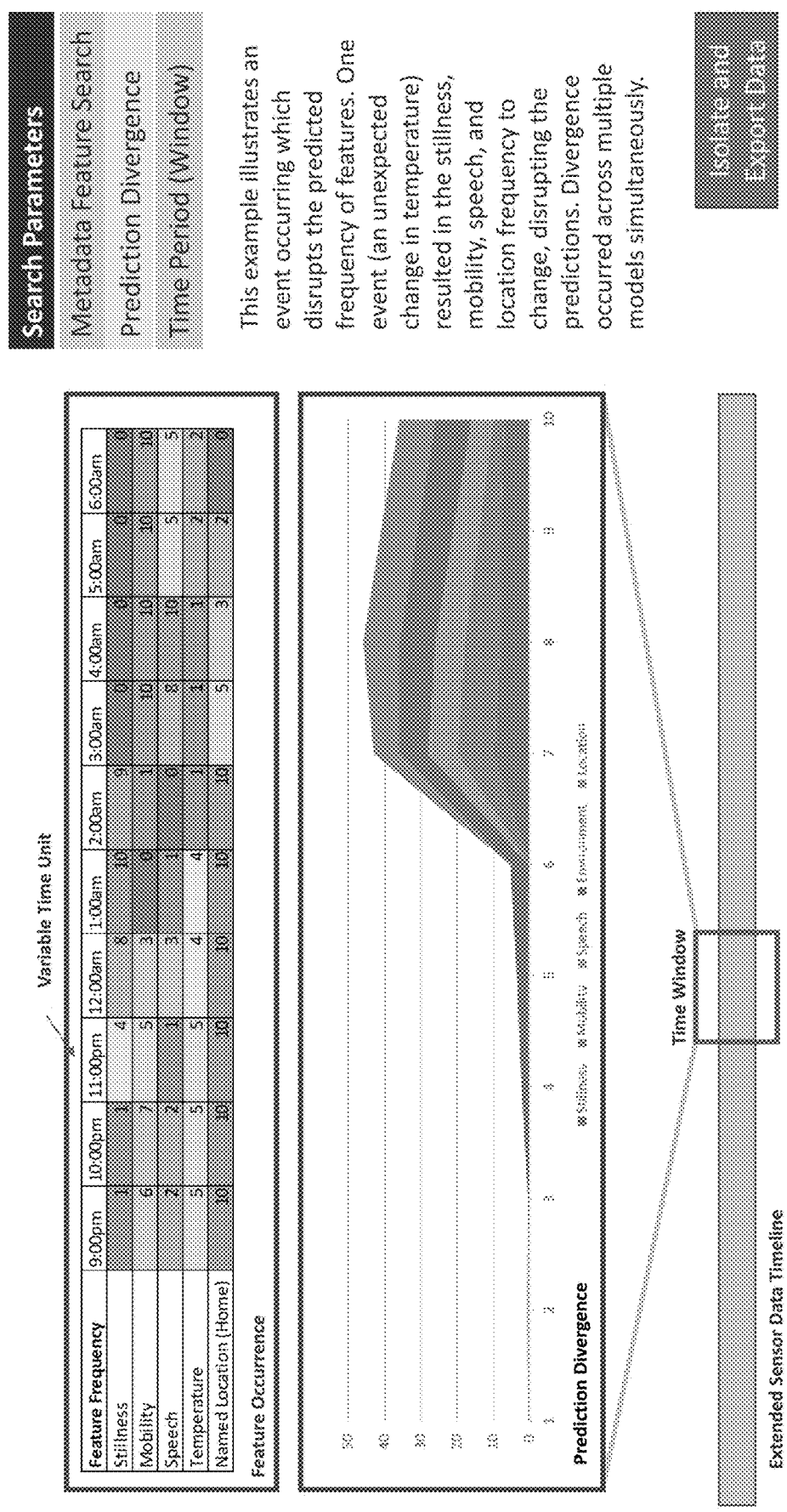
Fig 23. Example Index Visualization and Search Interface (Predictions)

SYSTEM AND METHOD FOR INDEXING LARGE VOLUMES AND DURATIONS OF TEMPORALLY-BASED SENSOR DATASETS

SEQUENCE LISTING OR PROGRAM

Not Applicable

TECHNICAL FIELD OF THE INVENTION

The present invention relates generally to a system and method to capture and interact with large volumes of machine generated sensor data. More specifically, the present invention relates to a system and method to index and represent temporally-based digital sensor recordings for the purposes identifying subjectively important actions, interactions, and events which may occur over extended periods as represented within large datasets.

BACKGROUND OF THE INVENTION

In this digital age, sensor-based data has become significantly more prevalent and now represents a growing minority of all data created and stored. Sensor data differs from human-generated data in that its form, manner, and contents are defined specifically through the hardware and software of one or more mechanically based sensors which are tuned to detect changes in physical phenomena. This might include light-based sensors used to record images and videos, sound-based sensors used to capture audio, or environmental sensors used to record such measurements as temperature, humidity, magnetic fields, air quality, or any other measurable physical characteristic.

To capture and represent these sensor measurements, systems typically obtain a high number of samples to produce a record which has sufficient fidelity for later analysis and review. Datasets intended for human experiential consumption typically capture frequencies of sound and light which correspond to or are compatible with a human's sense capacities, such as human audible frequencies of sound (the audible range) and human visible frequencies of light (the visible spectrum). In some instances, broad spectrum sensors such as those capable of detecting ultra-high or ultra-low frequencies of sound, radar waves, infrared light, and microscopic or telescopic phenomena beyond the range of human perception will capture and convert this data for human representation within their sensory ranges.

Most such systems implement encoding and storage methods to convert digital or analogue sensor readings to specific data structures and preserve them to solid-state media for later analysis. These methods can generate significant amounts of data and can require large amounts of costly storage media. Modern advances in storage media technology have allowed storage capacity to grow exponentially over the previous decades, enabling the storage of ever-larger datasets. Storage capacity has recently followed a growth trajectory known as Kryder's Law, in which the capacity of storage devices and the achievable density of storage media doubles every several months. Sensor-based recording technology has leveraged this exponential increase in storage capacity to increase the number, fidelity, and most importantly the duration of sensor records, allowing for the creation of increasingly lengthy datasets.

These datasets can require large amounts of media for data storage. For example, 168 hours (1 week) of continuous audio recording with 44,100 samples per second, a bit-depth of 16, and two audio channels requires 106.7 gigabytes of storage (assuming a common uncompressed encoding format). As such, 1 terabyte of storage can hold approximately 1,574 hours of uncompressed audio. More complex datasets, such as image and video, require significantly more storage. At common video encoding rates, capturing a '4 k' video stream in uncompressed (RAW) format, 1 hour of video requires a roughly equivalent 105 gigabytes of storage. Modern compression methods have reduced data storage requirements by applying encoding algorithms which optimize storage with no or minimal impacts on data quality.

As storage media capacity grows exponentially and compression methods become more sophisticated, it is now possible for such recording devices to capture datasets continuously for days, months, years, or even decades. Presumably, along the course of today's technological evolution, there is no upper limit to the durations of data which can be captured with proper planning and configuration. This capacity to store ever-increasing amounts of sensor data changes the paradigm of how we build sensor-based systems. It is now possible to proactively capture valuable information through continuous recording and extract its contents once their value is known retrospectively. Large amounts of data are also required to build advanced systems which employ thousands or millions of data samples to train advanced artificial neural network-based processes.

These longform (long duration) datasets are enabling new types of analysis and discovery. Longform sensor data can contain comprehensive narratives and histories of individuals and events (such as complete biographical histories), capture unforeseen events (occurring without notice), incremental events (over long periods of time), and concurrent events (across multiple locations, sensor types, and systems). Features of interest within the data may be identified which only exist on extended time horizons, such as trends and changes which happen on long cycles spanning tens or hundreds of years. Longform data also enables the ability to capture non-obvious or non-sequential patterns of cause and effect which may be invisible when data is segmented or limited in duration.

However, this form of extended duration recording introduces significant challenges in identifying, categorizing, summarizing, and sharing the subjectively valuable data which lies within. Longer datasets do not inherently mean that the data is more meaningful, only that there is a greater likelihood that valuable information or intelligence may be contained within. The ratio of low value and high value data may become less optimal as additional low value 'garbage' data is accumulated. However, confidence increases that all essential data has been captured. To paraphrase the old expression, as the haystack grows larger, our confidence increases that the needle we seek is contained therein but so too does the effort to find it.

Locating these valuable data subsets within longform datasets can be difficult. This task commonly falls to humans who must manually parse the data to identify what is valuable based on their inherent skills and individual subjectivity. To perform this task, humans utilize their inherent abilities of pattern recognition, classification, recall, and the application of their own objective and subjective scoring measures. However, this proficiency does not scale well. Humans often lack the attention, focus, interest, and sheer longevity required to review such large amounts of data. Modern datasets are already becoming too lengthy for any practical human review and will easily begin to extend beyond any one person's lifespan.

This challenge is amplified in part by how sensor data is represented. Present means of representing sensor-based datasets like audio and video are deficient in providing meaningful insight or intelligence about its contents or where a human should focus their attention. Audio for example is commonly represented by a 2-dimensional waveform image which contains amplitude on the Y axis and time on the X axis. Frequency is then interpreted in the width of the waves represented by a single line. Alternately, audio is sometimes represented as a spectrogram (produced commonly by an algorithm known as a Fourier transform) which places frequency on the Y axis, time on the X axis, and uses a false color heatmap to represent the amplitude of each frequency. A year of stereo audio for example contains 2.78 trillion samples, far too many to be represented in any detail visually on a modern device. Waveform or spectral analysis becomes very difficult to represent across a very large time scale, nor do these visualization methods provide a representation of the regions of subjective value within the dataset. Finding the subsamples of data with subjective human value is not aided by such means of representation. These challenges exist for the analysis and visualization of any time/amplitude sensor type of which there are many (biometric sensors, environmental sensors, electromagnetic sensors, motion sensors, etc.). While these methods are descriptive of the objective characteristics of a limited data sample, they do not scale to large datasets, nor do they contain clearly human-readable indicators of what may be valuable within.

More complex multi-dimensional datasets such as those representing video content suffer from similar challenges in representation. As each video frame contains a 2-dimensional array of pixels, each pixel represents the intensity and frequency of light, and each sample (frame) represents a moment in time (a fraction of a second), there are few meaningful ways of visualizing the contents of a long (hours, days, months) video record. The common method of representation is to provide single still image samples (sometimes known as 'thumbnails') at intervals and display them visually in sequence. Hours of video may be summarized with dozens of extracted thumbnail frames. It is then up to a human to make a subjective determination as to whether these samples are meaningful enough to justify narrowing in on a subset. If so, the reviewer is required to narrow the time period of inquiry and repeat this process numerous times until a subsample of video data can be reviewed, isolated, and extracted. For longform data, this method is subject to numerous failures. This visual representation of sampled thumbnails is not adequately representative to allow a human to determine whether the data contains information of value. The sampling rate makes it highly likely that important content will be missed when viewing large datasets and there will be large spans of time not represented between samples. Subtle changes in data are difficult or impossible to ascertain from these limited samples. Associated data, including audio, is not represented visually. Correlated datasets in other formats cannot be processed in this format, making comparative analysis difficult. As such, any method of sampling applied to any longform dataset will always introduce the risk that the sample rate is too infrequent and valuable data may not be displayed.

Due to these deficiencies, human efforts must be applied to sit and manually parse each dataset individually, making the task of data analysis highly time consuming and challenging. The individual human brain becomes the filter to determining which sections contain value. Each reviewer of such data may be seeking highly subjective information from this data based on their area of interest. For example, a collection of 1,000 audio recordings taken in as many separate locations over the duration of a year will result in 1,000 years of data to be reviewed. Depending on the interest of the reviewer (user), it will be impossible to isolate the specific subjects of their interest. Environmental researchers might wish to use the data to identify the specific occurrences of weather events, anthropologists and sociologists may wish to extract samples of human interaction, naturalists may wish to identify the patterns of birds and animals, biographers may wish to isolate the actions of specific individuals, engineers may wish to identify the movement of traffic along roadways, and so forth. The large dataset may contain all the data these individuals are seeking but without a means of isolating and indexing their respective areas of interest, it will be impossible to extract out subsamples of subjective value.

Additional challenges emerge due to in a human's limited ability to recognize, retain, and record temporal changes in longform datasets. Large datasets may contain and represent changes which may occur over an extended time horizon and at a variety of time scales. For example, a decade of temperature data will identify a wide variety of changes. Minute by minute, small fluctuations of outdoor temperature will occur due to local phenomena, such as the movement of air and the presents and absence of cloud cover. Hour by hour, larger patterns of change will occur as the rotation of the earth relative to the sun causes the rise and fall of daily temperatures through day and night. Day by day, this pattern repeats with minor changes which compound into seasonal temperature changes, represented in an annual cycle of change. It may require decades of such analysis to identify even more minute changes which result in profound impacts, such a global rise in average temperatures year over year. If the data were to be reviewed in real time, the years of continuous monitoring would exceed the human ability to track and parse this information cognitively. For data of objective value, mathematical methods of analysis such as the numeric averaging and monitoring of daily temperature minimums and maximums allow for the summarization and representation of data, such as a simple graph showing year over year average temperatures.

Summarization however has significant downfalls in how it can represent specific data subsets. An average of the audio amplitude over a year tells us little about its contents or its subjective value. An average of the color values within a year of video tells us nothing of the events it is depicting. While some limited analytical interest might be derived by such analyses, summarizations provide no ability to identify and extract out the areas of highest interest or focus the viewer toward the truly 'valuable' key events contained within these datasets. Human cognition is insufficient to identify and analyze large and complex datasets and present digital methods are insufficient to extract subjective value. As a result of these limitations, humans typically underutilize large datasets and ignore their value in representing meaningful and valuable insights into our lives, environments, and interactions.

To leverage the value of longform datasets, a system and set of methods is required to create indices for the dataset which can be used to direct human attention and detailed analysis. An index serves as a marker which identifies a data subset which may contain elevated value due to its contents. It may mark the beginning, middle, or end or a range of data. Indices may exist within a single dataset, identifying features within a single sensor stream, or across multiple datasets. Indices may be created for sensor data and against metadata, additional generated data which is created to describe the contents of the sensor data. For indices of longform data to be valuable, they should identify areas of heightened individual or societal subjective value.

While subjective value may change by individual, it may be generalized that human interests are largely centered around events of significant novelty and change. Novelty may refer to patterns and events which have never occurred within a timespan, such as a new experience and interactions. Novelty may be the first time you ever saw the ocean, a new experience, or the birth of your child, the introduction of a new person, or any other event which has limited or no historical precedent within an individual's memory. Novelty exists also on a diminishing scale whereby the degree of novelty diminishes through exposure. Change refers to any interruption in a predictable pattern of events, even if the specific event is not new. An interruption could an unexpected event which disrupts a schedule, such waking up at a new time, a habit change, or moving to a new location, an environmental change. The specific features of these changed events may have been experienced before, but the patterns of how they typically are manifest are altered. Changes may be temporary or permanent, with the magnitude, multiplicity, and permanence of change driving its noteworthiness.

Using novelty and change as the two most relevant indicators of potential human importance, it is possible to describe a system which automatically recognizes, indexes, and represents regions of heightened potential within longform datasets to optimize the identification of subjective value. Such a system would implement several of the key methods that human utilize in their identification of subjective value. The first method implements the categorization and retention of features within a dataset, a process known as pattern recognition. The second method identifies occurrences of features which defy a predicted set of patterns. The third summarizes such events into narrative accounts, synthetic descriptions which extract and represent the most important contextual and related events together for the purposes of expedient search, representation, and communication. The fourth identifies patterns, changes, and narratives which correlate to one another, identifying patterns of cause and effect or coincidence across multiple datasets. By applying these methods across variable time scales and datasets, the system generates a collection of indices which highlight specific regions of heightened potential thereby optimizing the manual and automated identification of potentially valuable data within longform sensor data.

Three primary index times are generated: novelty indices, divergence indices, and narrative indices. Novelty indices are created with new features and patterns are identified within a dataset and a specific timeframe. Variable timeframes may indicate the first identification of a specific data feature on a particular day, month, or even ever. Feature indices may also be used concurrently. The number of new patterns within a bounded timespan can be used as a multiplier to calculate the value of the change and therefore its potential subjective value. The coincidence of new features across multiple sensor types provides another indicator of potential interest.

Divergence indices occur when there is the delay, interruption, or failure of one or more predictable patterns of events. Divergence indices are created when sensor data fails to contain a set of features which would commonly be expected to occur. The failure of multiple predictions within a bounded timespan (coincidental events) can be used to multiply the importance of these indices. Like novelty indices, failures across multiple datasets may also be indicative of periods of heightened subjective value.

Narrative indices apply the textual categorization of features and patterns and are used to produce linguistic structures. For example, if audio data contained features which were pattern recognized as the sound of a doorbell chime followed by numerous instances of a dog's barking, the metadata generated of these events would enable the simple synthesis of a narrative description. Such a set of temporally related features could be described lexically as "At 3:09 pm on Monday, the doorbell rang which caused the dog to bark repeatedly." Such narrative descriptions provide a means of producing human understandable indices toward a large dataset which might have otherwise contained hours of subjectively useless information. These narrative forms a means of indexing the data in a way which is human readable and keyword searchable using linguistic tags.

The methods above provide a means of optimizing human analyzing by providing a set of derived indices which highlight the occurrence and absence of specific features and patterns within a dataset. Instead of visualization representations of the objective values of the sensor data, the end user instead utilizes these indices as a graphical representation to optimize their search, evaluation, and selection of valuable data subsets. Such indices also provide a means of optimizing any variety of system-based searching and summarization methods which may perform these tasks in an automated fashion, including the emitting of events when specific scenarios are identified as triggers to activate other modules or systems.

Hence, an improved system for identifying and indexing occurrences or regions of heightened subjective value to optimize the search, summarization, isolation, abstraction, and analysis of longform datasets. The method taught by the present invention will be a significant enhancement over any other method of indexing and identifying the subjective value of sensor data that is available.

SUMMARY OF THE PRESENT INVENTION

This method and system of the present invention breaks down into three primary parts: sensor-based data collection and storage, data classification and indexing, and interaction a digital interface.

The modules in this device include one or more multimodal sensor devices and information storage devices using existing digital media storage methods and systems. These modules are augmented using a novel configuration of algorithm and neural network-based processes which enable a pattern recognition engine and an index visualization interface which provides a means of end user interaction with one or more longform datasets by means of generated indices.

There are several specific methods and processes within this novel system which are believed to be the most unique and most likely to support the patentability of the system. These processes resolve the shortcomings of the existing state of the art identified above.

Continuous and diverse sets of sensor-based data are gathered via a range of hardware and software devices. This multiplicity of sensor sources and types provides the volume of data required for the training and operationalization of sophisticated neural network models without extensively relying on external and potentially biased training datasets.

Neural network-based classification models are generated and applied to create a comprehensive categorization of features within a dataset and the production of descriptive metadata. The resulting metadata enables the creation of indices which highlight periods of novelty which may translate into heightened potential for subjective value.

The indexing of features within the sensor data presents a means of creating predictive algorithms which anticipate the likelihood that these features will be identified within a dataset. When predictive algorithms degrade or fail, and especially such events occur across multiple datasets, new indices are created which highlight areas of significant human interest. By generating indices for these moments or periods of divergence, the system can identify, present, preserve, and share these events as a set of subjectively valuable data subset to optimize the search and review of sensor-based datasets.

The joint application of feature classification and the indexing of predictive model degradation provides a sophisticated means of searching for data subsets using a combination of qualitative and quantitative search terms which may describe the presence of a feature, the frequency or amplitude of its occurrence, and the magnitude of any related indices present within the metadata. This provides a sophisticated method of structuring queries against longform sensor data to optimize the extraction of intelligence form data subsets.

The visualization of sensor datasets using the derived indices and metadata as primary means of representation provides an optimal way for both human and automated search and extraction methods, significantly increasing the value of existing and future datasets while decreasing the time required to perform these actions.

While the objective of the present invention is to teach an overall novel system, these modules specifically differentiate this configuration of features and assist in making this invention novel and non-obvious in view of the prior art.

The method taught by the present invention significantly enhances the ease and speed by which valuable subsamples can be identified within longform datasets to support their extraction and distribution.

The method taught by the present invention utilizes pattern recognition models to produce descriptive metadata of features within sensor data.

The method taught by the present invention creates indices where novel features are identified within one or more sensor-based datasets.

The method taught by the present invention creates indices by monitoring the occurrence of temporary or permanent degradation or failure of predictive models as a means of identifying eras of heightened change.

The method taught by the present invention creates lexical narratives from the defined metadata categories as a means of identifying and searching for specific content which would otherwise be non-obvious within a dataset.

The method taught by the present invention enables the visualization of sensor data with these subjective indices to produce a sophisticated means of interacting with sensor data.

The method taught by the present invention facilitates the searching of subjectively valuable events using lexical classifications, qualitative terms, and quantitative terms.

The method taught by the present invention may be applied to optimize the indexing of various types of sensor data making it highly applicable for many different end user professions and interests.

Definitions

"Application software" or "software" is a set of one or more programs designed to carry out operations for a specific application. Application software cannot run on itself but is dependent on system software to execute. Examples of application software include MS Word, MS Excel, a console game, a library management system, a spreadsheet system etc. The term is used to distinguish such software from another type of computer program referred to as system software, which manages and integrates a computer's capabilities but does not directly perform tasks that benefit the user. The system software serves the application, which in turn serves the user.

The term "app" is a shortening of the term "application software". It has become very popular and in 2010 was listed as "Word of the Year" by the American Dialect Society.

"Apps" are usually available through application distribution platforms, which began appearing in 2008 and are typically operated by the owner of the mobile operating system. Some apps are free, while others must be bought. Usually, they are downloaded from the platform to a target device, but sometimes they can be downloaded to laptops or desktop computers.

An "End User" is any person registered to use the computer system executing the method of the present invention.

"GUI". In computing, a graphical user interface (GUI) sometimes pronounced "gooey" (or "gee-you-eye")) is a type of interface that allows users to interact with electronic devices through graphical icons and visual indicators such as secondary notation, as opposed to text-based interfaces, typed command labels or text navigation. GUIs were introduced in reaction to the perceived steep learning curve of command-line interfaces (CLIs), which require commands to be typed on the keyboard.

An "Index" is any generated data which identifies one or more locations of a feature or occurrence within a dataset.

"Metadata" is any data generated which describes one or more characteristics of or within the recorded data of invention.

A 'Model" is a data categorization or generation script, code, or algorithm, typically configured as a neural network, capable of producing either generated data or metadata.

A "Neural Network" (also known as an artificial neural network or ANN) is a computational process whereby numerous inputs are accepted into a function (called the input layer), processed through a series of steps (called hidden layers), and resulting in one or more outputs (called the output layer). Neural networks commonly have activation functions which control the amplitude and form of the outputs.

A "Sensor" is an electronic means of capturing real-world events and interactions, such as physical interactions, electromagnetic radiation, or forces.

"Training" is a process of refining the weights of neural networks by providing labeled or unlabeled data and evaluating the results. In an iterative fashion, the weights within the network are adjusted to optimize the output of the network.

A "web application" or "web app" is any application software that runs in a web browser and is created in a browser-supported programming language (such as the combination of JavaScript, HTML and CSS) and relies on a web browser to render the application.

"Wi-Fi", also spelled Wifi, WiFi, or wifi, is a local area wireless technology that allows an electronic device to exchange data or connect to the internet, commonly using 2.4 GHz UHF and 5 GHz SHF radio waves. The name is a trademark name and is a play on the audiophile term Hi-Fi. The Wi-Fi Alliance defines Wi-Fi as any "wireless local area network (WLAN) products that are based on the Institute of Electrical and Electronics Engineers' (IEEE) 802.11 standards". However, since most modern WLANs are based on these standards, the term "Wi-Fi" is used in general English as a synonym for "WLAN". Only Wi-Fi products that complete Wi-Fi Alliance interoperability certification testing successfully may use the "Wi-Fi CERTIFIED" trademark.

BRIEF DESCRIPTION OF THE DRAWINGS

The accompanying drawings, which are incorporated herein a form a part of the specification, illustrate the present invention and, together with the description, further serve to explain the principles of the invention and to enable a person skilled in the pertinent art to make and use the invention.

FIG. 1 is an overall composition of the present invention.

FIG. 2 is an MSD Block Diagram of the present invention.

FIG. 3. illustrates Data Transmission Types and Protocols of the present invention.

FIG. 4. illustrates ISD Block Diagram of the present invention.

FIG. 5. illustrates a PRE Block Diagram of the present invention.

FIG. 6. illustrates PRE Algorithms of the present invention.

FIG. 7. illustrates PRE Neural Networks of the present invention.

FIG. 8. illustrates a PRE Gross Feature Analysis (Audio Example) of the present invention.

FIG. 9. illustrates a PRE VSSD (Audio Example) of the present invention.

FIG. 10. illustrates PRE Fine Feature Analysis (Audio Example) of the present invention.

FIG. 11. Illustrates PRE Fine Feature Analysis (Image Example) of the present invention.

FIG. 12. Illustrates PRE Multiple Characteristic Extraction and Occurrence Measurement of the present invention.

FIG. 13. illustrates PRE Metadata Classification Indices of the present invention.

FIG. 14. illustrates PRE Metadata Narrative Indices of the present invention.

FIG. 15. illustrates PRE Model Visualization of Characteristic Occurrence Identification Over Time of the present invention.

FIG. 16. illustrates PRE Multi-Model Consensus Divergence of the present invention.

FIG. 17. illustrates PRE Model Temporary Divergence vs. Permanent Divergence of the present invention.

FIG. 18. Illustrates PRE Model Performance Peaks and Plateaus of the present invention.

FIG. 19. Illustrates PRE Models Divergence Over a Lifetime of the present invention.

FIG. 20. illustrates Layered Analysis Process of the present invention.

FIG. 21. illustrates IVI Block Diagram of the present invention.

FIG. 22. Illustrates Index Visualization and Search Interface representing Feature Indices of the present invention.

FIG. 23. Illustrates Index Visualization and Search Interface representing Prediction Divergence Indices of the present invention.

DETAILED DESCRIPTION OF THE INVENTION

In the following detailed description of the invention of exemplary embodiments of the invention, reference is made to the accompanying drawings (where like numbers represent like elements), which form a part hereof, and in which is shown by way of illustration specific exemplary embodiments in which the invention may be practiced. These embodiments are described in sufficient detail to enable those skilled in the art to practice the invention, but other embodiments may be utilized, and logical, mechanical, electrical, and other changes may be made without departing from the scope of the present invention. The following detailed description is, therefore, not to be taken in a limiting sense, and the scope of the present invention is defined only by the appended claims.

In the following description, numerous specific details are set forth to provide a thorough understanding of the invention. However, it is understood that the invention may be practiced without these specific details. In other instances, well-known structures and techniques known to one of ordinary skill in the art have not been shown in detail in order not to obscure the invention. Referring to the figures, it is possible to see the various major elements constituting the apparatus of the present invention.

Now referring to Figures, the embodiments of the present invention are illustrated.

100—Multimodal Sensor Device (MSD)

The multimodal sensor device (MSD) provides a means of collecting and processing sensory information. MSDs are commonly configured in a multimodal sensor device array (MSDA) and function in parallel to capture data of one or more types or within one or more environments. The most common environment would be the end user's home environment, but could reasonably extend to a vehicle, workplace, outdoor environments, public spaces, or anywhere the end user spends time. A MSDA may be split geographically over large areas and utilize communication networks to transmit data for consolidation and processing.

A digital microprocessor and hardware. An MSD possesses one or more microprocessors to assist in the gathering and digitization of sensory information. MSDs are digital devices, using encoding methods to record data to storage media. MSDs possess several capabilities including but not limited to computation, network communication, temporary or long-term data storage, power and charging capabilities, digital and analogue input pins to receive sensor information from peripheral devices, noise filters, wired connections, including UART, USB, and serial connections, lights, and onboard sensors including environmental sensors.

Peripheral sensors and devices. Each MSD contains one or more peripheral devices, typically sensors, which are responsible for collecting environment information and converting this to either analogue or binary signals. Analogue signals are read as a variable voltage input which corresponds to a number within a range (such as 0 to 4095) whereas digital signals are binary and either 'high' voltage or 'low' voltage but alternating rapidly to represent binary numbers (typically high voltage states represent a 1, low voltage a 0). Peripheral devices may include local storage media, such as SD Card or PSRAM memory chips as an example. Peripheral devices employ one or more communications protocols including but not limited to I2S, I2C, SPI, USB, UART, analogue to digital converters, and digital to analogue converters.

Each MSD possesses one or more power sources, typically a rechargeable battery or a direct current (DC) power source. Incoming power may be regulated to be delivered at one or more specific voltages (typically a nominal 3.3 v or 5 v) to meet the requirements of the microprocessor and its associated hardware. When a battery is provided, it is typically recharged via a charge controller and voltage regulator to meet its specifications. Power conversion when required is typically via a power supply, a low dropout regulator (LDO), or a buck converter which may be internal or external to the MSD. Current is regulated to ensure that the microprocessor and peripheral devices receive adequate power. A combination of capacitors, inductors, resistors, or other methods are used to regulate power flow and reduce rapid and undesirable changes in current levels which may result in the degradation of performance.

Firmware and software. Each MSD is configured with firmware which is loaded over a wired or wireless connection to the device and saved in memory. The firmware controls the functioning of the microprocessor, the control of data input and output pins, the storage of information, and the operation of the physical features of the device. The device may also be loaded with an operating system firmware or software, such as a Real Time Operating System (or RTOS) which can be used to configure the reservation and utilization of system resources and processor computation. The firmware and software control the acquisition of data and how it is transferred to other devices.

Acquisition of sensor data. An MSD can capture data from numerous types of sensors including but not limited to: Audio data; Motion data; Timing data; Touch sensor data; Proximity data; Environmental data; Digital signal communication data; Battery data; Network connectivity status and availability; Network communications latency; External device connectivity status and data; Mesh communications; and Synching and connectivity with charging stations which may bear a unique ID and a known physical location.

Audio data is gathered using one or more high-fidelity microphones. This microphone captures acoustic data (minute changes in air pressure caused by sound waves) and transfers it into electronic signals. The data from the microphone is transmitted to a buffer in the microprocessor for processing and transmission. The MSD is configured to capture audio for extended of periods which may span hours, days, months, or longer. Audio data is typically collected using a high sample rate (16 kHz to 44.1 kHz) in mono or stereo fashion.

Motion data is gathered using an accelerometer, magnetometer, compass, gyroscope, or a combination of these motion sensors which can determine rotation, bearing, motion vectors, vibration, acceleration, or other gross or fine movements. Motion data is collected as arrays of data which consist of X, Y, and Z motion, rotation, acceleration, and bearing as it can be deduced by the combination of these sensor measurements.

Time data is gathered using both the internal clocks within a microprocessor unit or externally functioning as a peripheral device. Time data can also be gathered using a request across a communication network to an accurate time recording device capable of returning this information, such as an atomic clock, or wirelessly using remote satellite information from such services as GPS or through protocols such as LoRa or other satellite systems.

Touch sensor data is gathered using one or more capacitive touch sensors made available for human interaction. Capacitive touch data is captured in a binary fashion where the start, continuity, and cessation of touch are recorded with the times that they occurred. Capacitive touch sensors may be arranged to capture a discreet touch event or in an array to capture motions (swiping, sliding, rotation) where an end user's hand or fingers may move across multiple sensors in succession and be interpreted as motion. Non-capacitive methods, such as resistive touch, may also be used to achieve similar results.

Proximity data is gathered using one or more optical time-of-flight sensors, commonly referred to as LIDAR. LIDAR functions by measuring the interval of time it takes a stream of photons to leave an emitter, travel to and reflect off an object located some distance away, and for the photons to be detected by a receiver. Based on the constant C of the speed of light, the time from emission to receipt can be used to develop accurate distances from a sensor to an object. LIDAR data is used to detect the proximity, approach, and possession of the multimodal sensor by the end user, and to determine the nature of the environment around the device. This includes detection if the device is sitting in an open area or whether it is contained within the end user's clothes (such as a pocket) or other enclosure. In some instances, LIDAR data can be used to determine the reflectivity (albedo) of an object based on the strength of the signal returned to the receiver.

Environmental data is gathered from a temperature sensor which may capture values from both the multimodal device and or its proximate environment. Temperature data can be used to determine the environment where the MSD is located and provides an indicator of the proper functioning of the device's hardware features. Air pressure, humidity, and air quality may also be tracked with designated sensors to further record or identify an environment.

Digital signal communication data is transmitted using various protocols including Wi-Fi, LoRa, and Bluetooth. The measurement of signal strength, the digital identification of wireless networks, the degree of interference of signals within an environment, the loss of packets during attempted transmission, the time of response from another wireless device (round-trip latency) can all be used to develop a clear understanding of the location of the device relative to other humans, their homes, their appliances, and other devices. Wired communication protocols including ethernet and RS-232 may be applied when devices are so equipped and wireless communication is not an optimal implementation.

Battery data is gathered by identifying the status of battery charge or and the voltage of the battery as power is consumed relative to the maximum and minimum known voltage permitted by the battery or control circuitry. The measurement of battery voltage data provides indication of the usage of the device (how long since last charge). The rate of decrease of voltage compared to the activation of the sensors provides information on the battery performance decay over time and when the user of the device may have to charge or replace the battery.

The availability, identification, and strength of wireless networks is a clear indication of location and context of the device relative to other fixed or ambulatory wireless network devices, including routers or other equipment. Detecting network connections which have a named SSID (network ID) and MAC address provide a high degree of confidence of relative proximity to a known or unknown location. Signal strength provides a means proximate distance measurement (close, midrange, or far) from fixed locations with known transmitters.

Network communication latency of both local wireless communications to a router or other devices within a mesh configuration or the latency across a network are also indicators of contextual geographical location and the interstitial infrastructure configurations between the sensors and their endpoint connections. Consistent network latency may indicate that there is a long geographical distance between the multimodal sensor and the information storage device (ISD) in section [200] where the data is being received. Intermittent latency may indicate external network events (lots of users on the same network accessing limited bandwidth). Network packet loss may indicate an intermediate wireless protocol with inconsistent network connectivity or poor performance.

External device connectivity status and data is generated where one or more MSD can communicate with an array of external devices and peripheral sensors using common wireless protocols. When this occurs, data is transferred between the devices across a network or via a peer-to-peer protocol like Bluetooth. The multimodal sensor can receive or transmit to these devices. It may also be configured to pass on information from these devices wirelessly on their behalf. For example, it may receive a Bluetooth signal from a nearby peripheral and then pass on this data across a Wi-Fi, cellular, or LoRa network to the ISD.

Mesh communications and the presence of other compatible devices capable of forming a peer-to-peer connection occurs when an MSDA, operating in a mesh configuration, can determine which other devices are present on the network, their nature, their operating status, their function, and their approximate distances due to signal strength. The gain or loss of mesh nodes within a network may indicate movement of sensors in and out of the network range.

Additional peripheral devices. While the above sensors are standard in any configuration or embodiment of the multimodal sensor, an MSD may also be configured or manufactured with additional optional peripheral sensors which are contained within their enclosure or attached via a wired or wireless connection. This includes but is not limited to:

Image or video capture via an optical sensor (camera) enable where images may be captured and transmitted or processed and analyzed locally on the multimodal sensor using image recognition algorithms. Image data may be compressed prior to transmission in lossless or 'lossy' formats. Analyzed images may be transmitted with full or reduced resolution. Metadata from the image analysis may be transmitted together or separately from image data.

Additional environmental sensors can also be attached via standard connections to the microprocessor. Optional air pressure, magnetic field, humidity, pH, and other sensors can be added to the device to gain a more multifaceted analysis of environmental conditions. Environmental features can be used to determine the location context of the end user as well as the physical context of the device (inside or outside).

Communications and protocols. The data captured by the MSDA is transmitted over a wired connection or wirelessly to an information storage device [200] to be stored, indexed, and analyzed.

The data that is transmitted from the multimodal sensor may be encoded in a variety of industry standard or custom/proprietary formats. Sensor data is most likely to be transmitted using a structured format, such as JSON or XML, which bundles sensor values with important metadata such as relative date and time (often specific to the millisecond or microsecond). Data from third party peripherals is likely to be encoded using the preferred encoding method of that peripheral, potentially augmented by an MSD with additional metadata. Audio and image data may be transmitted in raw values or may be encoded using standard methods such as MP3, WAV, RAW, PNG, JPG, OGG, MP4, or other encoding protocols.

An MSD may adopt several standard or custom transmission protocols including, but not limited to, TCP/IP, UDP, mesh broadcast, LoRaWAN, or WebSockets, depending on the nature of the data and the required transmission performance. Some protocols like TCP/IP can be evaluated for packet loss, as per above, while other protocols such as UDP and mesh broadcast do not resolve this information (packet loss is not measured to enhance transmission speed).

Edge data analysis and optimization. The MSD may contain software or firmware which enables the analysis of data on the device's microprocessor prior to transmission. For example, algorithms or machine learning models, such as neural networks, can be loaded on the device and executed as processes to evaluate the data being collected by the sensors and an initial analysis of the presence of gross or fine features (as identified by the pattern recognition engine (PRE) in section [300]). This analysis is recorded as metadata which is transmitted to the ISD. Additionally, it may also be used to optimize the operation on the device, including but not limited to optimizing power utilization and recharging requirements, performance, network traffic, and data storage requirements on the ISD.

Edge computation for data variability analysis. The operation of an MSD may be optimized by utilizing data variability analysis of the datasets collected. If a multimodal sensor device were capturing one or several data streams, such as audio, motion, image, network, and environmental data, each of these streams of data may be analyzed for the relative variability of their data's maximum and minimum ranges within a period. As examples, the variability of sound is measured in decibels which records the degree of amplitude of the sound wave, motion is measured by the rates of acceleration, rotation in magnetic field or gyroscope readings, images in light intensity. If the variability is low, meaning the sensors are returning data which is relatively consistent from one sample or set of samples to the next, this would indicate low data variability. In real world terms, this might represent a quiet space, an unchanging image, a static set of wireless signals, a lack of significant movement, or a consistent temperature or environmental information.

An MSD may apply this analysis to optimize the flow of information that it transmits across the network, reduce its sample rate from its sensors, or only resume transmission with the variability of the data exceeds a specific threshold, such as when a sound is detected or the device is picked up and moved to a new environment. This will have the desired effect of reducing data transmission and optimizing the overall performance of the MSDA and all subsequent data processing activities within the invention. It may be desirable to continue to send a subset of metadata to identify that the device is still working and connected (known as a ping, or heartbeat) to identify to the ISD that the connection is still valid but that the data variability is low. This will help the end user by differentiating between lost or missing data and static data that is omitted to optimize performance.

Additional or reconfigured devices. It is to be expected that the MSD design, configuration, and implementation may require alteration to meet the needs of each end user. Any combination of sensors and modular devices may be used to capture a range of sensory inputs suitable for use with this invention.

200—Information Storage Device (ISD)

The information storage device (ISD) is a physical device connected to a local private network or a virtual device hosted on a communication network. A primary function of the ISD serves as a method of authenticating, receiving, storing, and retrieving data that is sent via any multimodal sensor device (MSD) [100].

Components. The ISD is equipped with one or more of the following hardware components: Microprocessor, Wired and or wireless data transmitter/receiver, Volatile memory (such as RAM), Data storage devices such as hard drives, Power supply, Optional peripherals such as input device(s) and or monitor screens, augmented or virtual reality interfaces The ISD is also equipped with one or more of the following software to permit its functioning, including: Operating system, Database, Web server software, and Messaging queue.

Upon network connection initiation with an MSD, the ISD receives device metadata including MAC address, IP address, local date/time, hardware characteristics, common alias, firmware version, public cryptographic key, as well as any metadata that has been assigned to the device during its configuration. ISD may authenticate each connecting device using one or more of these methods. When secure communication is required, standard cryptographic key exchange method is performed to enable a secure transport layer security (TLS) connection. The ISD returns an authentication token to the MSD for ongoing communications which is valid for a particular amount of time to reduce the overhead of authentication.

The ISD can receive data following several protocols, including but not limited to TCP/IP, UDP, and WebSockets. It can also receive data via standard HTTP connection or secured HTTPS connections or related FTP and SFTP protocols. The ISD can receive and transmit data on common web protocols including but not limited to the REST protocol and GraphQL protocol for device communication. The ISD can function as a WebSocket server, client, or repeater to relay data to external subscribing devices to specific data streams as well as specific modules within the invention.

Data that is received by the ISD is programmatically augmented with additional metadata, including the system date of the ISD, any known details about the connection including the latency of the connection, the method of authentication, or other relevant data.

The number and nature of MSD end points are dynamic and may change and adapt, evolve to new versions, be expanded with new features or firmware, cease to function, be replaced, or be turned off for periods of time. Metadata which records the nature, quantity, and configuration of dynamic sources is generated and recorded by the ISD. The addition of new data sources or the temporary or permanent losses of data sources all indicate a relationship with the end user's socio-economic capacity or their psychological engagement with the process of autobiographical capture identified in this invention, which can be expected to change over time.

The ISD stores the information it receives using a combination of temporary volatile storage (such as active memory or RAM) as well as long-term physical storage (such as traditional or solid-state hard drives or other durable digital media). The ISD may implement at any future point new data storage technologies which emerge to offer greater capacity, performance, durability, or reduced cost. Aging or failing media storage devices which are nearing or have exceeded their anticipated lifespan or warranty period can be substituted with new media storage devices, with data replication from one source to another to avoid unplanned failure and loss of data.

The ISD utilizes one or more database software applications which provide the means to capture data in a variety of formats, including but not limited to relationally (split into separate 'tables' which may be connected by unique values known as 'keys' which permit the future logical joining of data), as documents (structured hierarchical datasets which implement 'key' data descriptors and 'value' data value pairs), and/or graphs (data elements which are stored as 'nodes' and linked together with pointers known as 'edges' or 'links' which contain information about the relationship between the nodes), or any combination thereof. Additionally, ISD may store data as large binary objects, large text-based objects, or other means of aggregating data to be retrieved as one or more objects. The ISD may optionally use the file system of its operating system to also store files to a folder and file structure.

The ISD selectively implements and generates indices for the datasets received. An index is a summarization of stored data which can be loaded into active memory to facilitate the searching and retrieval of stored information. Additional indices of key features of the data may include its device of origin, data type, descriptive labels, text, time of receipt, and status.

Although the ISD has been identified as a device for simplicity's sake, it also can be configured to implement resiliency and data synchronization across multiple devices within one physical location or across a local or distributed network to maximize parallel processing and minimize the potential of irretrievable data losses. For example, two or more physical computers could be established to function in parallel, with a main device receiving data from external sources and any number of secondary devices mirroring the main device and serving as redundant backups. In the event of a performance degradation of the main device, or any device failure, a secondary device can be selected through an election process (a peer evaluation of relative speed, capacity, and network performance) and a different device designated as the main device and assume the function of the main ISD to all externally connecting devices, such as a MSDA. Similarly, the ISD may implement a process known as 'sharding' or segmentation to establish geographically separate instances which hold separate datasets.

Additional storage resiliency may also be configured for a single ISD or any number of ISDs working in synchronicity as identified above using storage methods such as RAID (or Redundant Array of Inexpensive Disks) which can be configured to save multiple hard disk copies in parallel or to permit the retrieval of lost data on one drive through a method known as 'striping' which stores sufficient redundant data on multiple drives to rebuild some or all lost data in the event of one of the drives becoming corrupted.

Several devices forming the ISD can also be configured to be geographically separated, such as across a network, and or virtualized by a third-party provider. Geographic displacement of various devices is a strategy to minimize the likelihood of loss due to catastrophic or interrupting natural evens, such as earthquakes, tornadoes, floods, or human-made events such as wars, sociopolitical strife, changing laws, climate change driven natural events, and relationships between regions. Several devices offering an ISD functionality can be configured for data replication. Less sophisticated storage devices can be used as simplistic backup methods. The ISD may also use distributed ledgers to disburse information across a large, self-managed network of participating nodes as identified in more detail below.

Storage of configuration data and history. The ISD stores configuration information, including authentication and end user access. It may also implement a standard open authentication method and permit third-party authentications for authentication and authorization. These methods are commonly referred to Open Auth, or OAuth, SAML, or other common authentication standards. The ISD stores all configuration data related to the operation of this system.

300— Pattern Recognition Engine (PRE)

The pattern recognition engine (PRE) performs a core set of functions within this invention by translating raw data within the information storage device (ISD) [200] into structured metadata using a variety of algorithms and machine learning methods, including but not limited to artificial neural networks.

Storage of metadata. The PRE produces metadata for several purposes including but not limited to the identification of features, patterns, predictions, and indices as well as the neural network models and the customization parameters for algorithms. The models are stored within the ISD and may be loaded, operated, and evaluated by the PRE's core functions. The metadata is typically created as structured data objects which are linked to the relevant datasets within the ISD. Metadata typically possesses time and date information to associate the classification with the source data. Metadata may be human readable text, such as labels, binary or numeric classifications of confidence against those labels, or other outputs which are not human readable classifications. Metadata generated by the PRE is commonly stored in individual files, relational tables, document structures, or in graph databases, depending on the nature of the original data and the nature of the metadata.

The metadata generated by the PRE forms the basis for the categorization of data within the ISD for indexing, searching, and interaction. The PRE processes data through numerous data processing steps. Because this invention is intended to analyze data in a highly continuous fashion for a long duration, decades or more, it is expected that the specific technical methods, such as the use of neural networks as identified below, will change as new methods are adapted and discovered. However, the general functions of extracting data and generating metadata for the purposes of classification, pattern recognition, and indexing are the core principles of the PRE and are the most relevant to this module of the invention.

Numerous types of neural network-based models. The PRE contains and produces a large, dynamic, and diverse set of neural network models which are trained and evaluated regularly against the data in the ISD. It is expected that over an extended timespan, such as the duration of the end user's natural life, the PRE will generate thousands of distinct pattern recognition and predictive models which are designed to produce numerous types of metadata for all types of data within the ISD. Models will be created through the analysis of data from single and multiple data sources. Training of models will also include variable time ranges from available data within the ISD. Models may be created for specific time-based subsets of data and used to measure their fall-off in performance as an indicator of the variability of data within a dataset. Other models will be created to be frequently or occasionally retrained based on the availability of new data and the requirements of the end user.

The PRE processes numerous data types, including audio, motion, sensor, time-series data. The PRE enables the analysis of dozens or hundreds of diverse data types and encodings within the ISD. While the specific protocols for extracting training and analysis data would vary across data types, the following methods within the PRE generally apply to all different data types. For example, some neural network configurations are optimized to work with feature recognition in images, some are optimized to work with sound pattern recognition, while others are best suited for environmental data such as motion data or location data. In numerous examples below, audio data is used to illustrate how the system functions as it represents both time-series data but also contains numerous dimensions which enables visual analysis and representation for illustrative purposes using standard graphical representations such as sound wave forms and full-color spectrographs. However, the use of audio analysis for explanatory and illustrative purposes does not limit the diversity of different data types which will be analyzed within the PRE.

Categorization of gross features within data using rules-based or neural network-based methods. The PRE applies multiple methods to evaluate data within the ISD and identify gross features within the data. Gross features refer to the values of data which may represent a change in state. For example, gross features in audio data may be areas of relative silence (low amplitude data) or areas where sound increases (amplitude increases). The silent area in this example would be one gross feature, while the period of noise that is detected would be another gross feature. In the process of gross feature categorization, the nature of what the data represents is not the primary focus, merely the identification of basic patterns which can be associated with time, area, volume, or other objective characteristics identified within the dataset. Audio will have periods of time where it is quiet and loud, depending on the interaction. Images will have areas where there are detectable edges, color patterns, contrasts, or artifacts. Multi-dimensional data may have features defined in 2, 3, 4, or more dimensions.

Algorithmic and neural network identification of gross features. Gross feature categorization applies both static algorithms as well as trained neural networks to perform this categorization. Algorithms are used to identify logic-based boundaries, such as a periods where there is a change in the amplitude of audio data values, the variability of motion in location data within a certain period, the presence of certain colors or color contrasts within an image (such as the 'vibrancy' of an image), to name just a few examples. Data subsets are fed into these parameter-based algorithms and when certain conditions are met, the function is triggered which identifies the presence of a feature. Similarly, the same algorithm or a subsequent algorithm can be configured to determine when that feature is no longer present within the dataset, marking the end of a feature. Algorithms may examine variable subsets of data and apply numerous mathematical or functional steps to generate feature metadata.

The use of neural networks for high data variability. Some datasets, like accelerometer motion data, are highly variable and change unpredictably based on circumstances which may make them difficult to assess using mathematical or logic-based algorithms. This is especially true in sensor data where there are many factors which can alter how data is recorded. In these situations, neural networks may provide a superior method for categorizing data.

Supervised learning neural networks. Some neural networks are configured through the evaluation by training datasets, accurately identify data samples which represent either features or boundary conditions. For example, a training set may contain extracted audio samples which represent one person or many people talking. If this training set is inputted into a neural network, and provided the sample size is sufficient, a neural network would establish a complex mathematical model that could accurately identify situations within the data which represented human speech within a degree of confidence between 0 and 1, with 1 representing complete confidence. Similarly, two neural networks could be trained to recognize the moments of transition between relative silence and the start of speech (when someone starts talking) as well as the transition between speech and relative silence (when someone stops talking). These transitions represent features within the data which a neural network would be well suited to identify.

Unsupervised learning neural networks. Alternately, some neural networks are created with unclassified data. The PRE utilizes unsupervised neural networks to classify features for which there may be no training data available. Instead of matching features to a predetermined set of classification categories, the neural network instead cluster features based on their similarity. Cluster groups are created which contain numerous classifications which exist within proximity to a notional centroidal point, with their degree of their alignment represented by their point in a cluster. Clusters may be multi-dimensional and may be grouped to define classifications based on numeric, hierarchical, probabilistic, or other grouping criteria. Unsupervised learning allows the PRE to identify potentially new features without previous definition of these categories within the ISD or PRE. Categorization can occur after the fact through the end user manually applying category parameters (such as labels) or through the comparison of features with external labelled datasets.

Variable duration data sampling. The PRE implements both algorithms and trained models to conduct variable duration data sampling (VDDS). VDDS is a mechanism of either analyzing large pieces of information in smaller datasets or synthesizing small datasets into larger ones. VDDS is a critical component to gross feature characterization because it generates sample datasets of the appropriate size to capture specific boundary conditions and features which can be analyzed for feature identification.

For time series sensor data, such as audio, the VDDS supports the classification of features by analyzing or synthesizing audio into different time ranges. For example, if you have 60 seconds of audio, you may want to know if this audio contains human speech. Fed through an algorithm or a trained neural network, you may detect that it does. However, you might not know how much speech it contained, or where in the dataset this feature was located. Practically, you may want to extract out all the periods of time where human speech is occurring so you would need to know when it started and stopped. In this case, the VDDS may extract out data in incrementally smaller segments from 60 seconds down to individual seconds and then evaluate these segments. You would then receive 60 results from your analysis (one for each second) which state the probability that this second contains human speech. Aggregating these results, you would then be able to determine the ranges of time where human speech occurred. Alternatively, the VDDS can extract out 60 1-second increments and feed them into an algorithm or neural network that recognizes boundary conditions where features start or end. Using this method, you would return a smaller dataset of all the 'start' conditions and all the 'end' conditions from which you could derive the periods of time when speech was occurring within the dataset. The PRE thus generates metadata which indicates the presence of a feature and the time (location) when that feature is found relative to the larger dataset. Finer grained VDDS analysis may produce more accurate identification of the location of the boundary conditions with the trade-off being that each smaller sample has less data to be analyzed which may make recognition more difficult. Thus, VDDS may encounter an operational floor by which the samples are too small to support accurate pattern recognition. By monitoring the 'failure' point of this VDDS sampling approach, the PRE identifies the optimal sample size for the accurate generation of metadata.

VDDS may also present longer periods of data for macro-feature analysis classification. For example, joining data samples together into a large dataset such as hours of audio would allow for the measurement and creation of bulk classifications such as "Quiet periods" occurring at night for several hours while the end user is sleeping, or "Active periods" during time where there is a relatively diverse and continuous number of activities captured within a period of time. The VDDS provides the same sort of analysis potential for all other sensory datasets where any dimension of data can be extracted from the whole. It may also be applied to images to develop a tessellated sampling of images to extract out bounded sample sizes.

Analysis of features for multi-feature analysis. The above process of feature analysis can also be applied to extract multiple features within the same dataset by applying various algorithms or trained neural network-based models. The 60 seconds of audio used in the example above may contain human speech, but it could also contain environmental sounds which could also be recognized. For example, it could contain 10 seconds of human speech followed by a dog barking, an appliance being activated, and a large truck passing by. The audio may also possess signature qualities which represent various environments such as an inside space, a vehicle, or an open-air exterior space. Multiple neural networks are applied to the same samples of audio at various durations extracted by the VDDS, resulting in multiple features being categorized within the dataset and their locations within the data adding additional metadata to be stored.

Fine feature analysis. Once gross feature analysis has identified the areas for further processing, fine feature analysis can be applied to further classify gross features down to specific features and translate the data within those designated time-ranges into relatively accurate and complete metadata to support the creation of metadata and novel indices.

In addition to sampling data based on its time, the VDDS may also sample data based on other characteristics such as amplitude, volume, intensity, etc. In this case of audio, this may be frequency and amplitude. For example, a fine feature analysis may wish to only sample data within a specific frequency range or amplitude range. The VDDS will sample the full dataset but return a sub-sampled dataset accordingly, a process known as filtering. Filters provide bounding thresholds and ranges for data analysis where data that falls outside these ranges may be excluded from the training or classification set of the neural network. An example of this in audio data would be high-pass, low-pass, and notch filters. These filters work by removing specified audio data whose frequency falls beyond a specified frequency range in hertz (Hz). A high-pass filter allows all high frequency signals to be kept while discarding all the low-frequency signals, while a low-pass filter performs the equal but opposite function. A notch filter performs both functions, establishing a low and high threshold and only permitting data within a specified frequency to be analyzed. The benefits of applying filters allow for aspects of the data to be classified independently. Again, in the case of audio, a high-pass filter could be applied to remove most of the human speech, which resonates at a relatively low acoustic frequency of approximately 0-300 Hz, varying typically for men, women, and children. A high-pass filter set to remove higher frequencies such as 400 Hz or above would largely remove the human voices and allow for fine feature analysis of the other noises within an environment, such as environmental acoustics for classifying rooms, appliances, or other devices within the data set. Similarly, applying a notch filter at specifically 60 Hz in a North American context would allow for the detection of electrical noises generated from any device powered by alternating current (AC). Such data would be indicative of devices and their relative location within an environment from the sensor and the end user, permitting analysis of the end user's activity and movement through a space.

Filters may be applied toward all data types. Image filters may similarly isolate certain colors to support feature analysis, increase or decrease the contrast of images, reduce or change the hue or saturation of colors, invert, convert to grey scale or black and white, or subsample the image (reduce its pixel resolution) to support faster analysis and classification to name just a few potential filters. Filters can also be applied to unstructured data, such as dropping out textual content that is irrelevant or over-represented to better establish context and narrative. Filtering may be based on algorithms with specific mathematical or numerical definitions (such as ranges) or can be based on neural network filtering which applies methods of selective data removal. For example, one neural network may be trained to classify and remove all 'background' information from an image, leaving only the foreground or human subjects for analysis. Another neural network may be trained to remove all foreground subjects and analyze only environmental context (sky, light, nature) to classify the local weather and estimate the environmental experience for the end user.

Reprocessing previously examined data. From time to time the PRE will re-analyze data after its models have been updated or enhanced through retraining or its algorithmic parameters adjusted. Newly created models or adjusted algorithms may provide incremental enhancements or in their ability to identify features within datasets. Reprocessing previously classified data provides an opportunity to glean any remaining features within the data, boost confidence in the metadata scoring, and to compare the performance of distinct model to evaluate overall whether confidence and accuracy have increased. The model is expected to produce different results with different degrees of confidence with each evolution of the neural network. If the measured performance of the updated model scores lower than previously generated models on comparable datasets, this can be an indication that the new model is not as good as the old model. The results of re-processing data will inform the PRE on the efficacy of its model creation processes, such as the most suitable number of data samples required for training of new models, providing opportunities for enhancements or refinements. This feedback mechanism provides the PRE a means to evaluate its performance and trigger continual retraining of models and reclassification of data.

Training models from external sample datasets. The PRE may be configured to incorporate external datasets for the purposes of training robust neural network models. Depending on the available sensor data, it may take a long time for the end user to generate sufficient data to produce a robust training sample for neural network development which results in highly accurate classification and prediction. In such cases, it may be required to import external datasets to augment these models to produce systems capable of recognizing and classifying features within any dataset.

Augmentation or resolution of data with encyclopedic and contextual knowledge datasets. Data within the PRE will commonly be augmented with knowledge datasets to provide classifications and labels to data based. For example, if the ISD receive and possesses extensive GPS data, consisting of longitude, latitude, altitude, and time, the PRE may recognize locations but lack the context to determine why the end user is there. To establish a narrative, external contextual knowledge datasets may be added to support the labelling of data. In this example, importing geographic information, such as open-source street map data or named features with known latitudes and longitudes will allow the PRE to label the datasets. A specific longitude and latitude can be resolved to be a building, with a type (office or residential), a civic address, image reference data, and so forth. This augmentation allows for far more intuitive data management and discovery by humans who possess similar contextual knowledge.

Training data generation and augmentation through data abstract and manipulation. In many instances, recorded sensor data may not contain enough diversity to ensure that the models learn to recognize all scenarios adequately. For example, a neural network trained to recognize a single image of a person may become proficient at recognizing that image but not the person contained therein in multiple contexts within a sequence of images or video. Instead, it is important that there are many pictures of that person, in many angles, in many lighting scenarios, making many facial expressions, and at various data sample sizes (resolution) to ensure the model can accurately classify the pictures of the person across a diverse number of scenarios. In short, the common patterns that the neural network learns must be varied enough to be recognizable within an acceptable range of situations.

Producing synthetic training data. To overcome these training challenges, the PRE applies several algorithms and functions to support the grow of training samples from limited data through sample abstraction. Image gross features may be extracted, rotated, blurred, noise or distortions added, color pixel data adjusted, mirrored, duplicated, skewed, or abstracted in any number of ways, with each abstraction joining the training data. Just as a human could recognize an image of the Eiffel Tower even if it were rotated, had its colors inverted, and dimensionally skewed by recognizing the features of its geometry and the patterns of its architecture, a neural network trained with adequately diverse training data is capable of learning and identifying the features which remain after the abstraction.

Data specific synthesis methods. Not all methods of abstraction of relevant to all types of sensor-based data. While an image might be reversed and still be recognizable, sound data would not likely be reversed. While an image might be rotated, sound frequency would not swap time for amplitude. However, the axial movement or rotation within motion data could swapped between axes, as it is quite common for the relative axes of motion data to change as the orientation of the sensor device changes in respect to the nature of the rotation and the force of gravity.

Additive data synthesis. Another method for generating training data for time-series sensors such as audio or motion data is to overlay segmented datasets and recombine them through additive functions. Extracting one person talking and overlaying other audio samples, such as other people talking, pets, nature sounds, environmental interferences, echoes, and entertainment programs will also diversify the ability for the neural network to recognize the features of the end user. While image data may not be commonly additively overlaid (known as double exposure), as this is not a common image effect, images may be tessellated, collaged, tiled, or blended, to create new scenes and new interactions for enhanced training. Applying these data distortion and abstraction methods will strengthen the feature recognition of the neural network and build more robust pattern recognition models.

Feature recognition. Once adequately sophisticated pattern recognition models are created to support feature recognition, they are used to parse all data types and develop a comprehensive set of metadata which describes the location, nature, and characteristics of each feature within their respective datasets. Each piece of generated metadata becomes a means of parsing longform data and developing insights into the frequency of each feature. The occurrence of the features provides a means of also indexing for novelty, whether contextual or global. Within any subset of data, features can be identified based on their relative degree of novelty. Each feature occurs for the first time in a dataset at some point, which marks an important index. When multiple novel features are recognized within a specific timeframe, this index or set of indices may be amplified in importance and be assigned a higher score. Similarly, a 'sliding window' temporal view may be applied to identify novelty within a limited timeframe, such as a day, month, or year, making novelty indices adaptive to the temporal scope of the end user's search criteria.

Cross-data contextual analysis. Some features also exist across multiple datasets or are comprised of multiple pieces of metadata. A novel feature may be recognized when there are concurrent, coincidental, or casual features which are observed across one or datasets in parallel or series. When these features correlate, specific events may be extracted and described based on this composite set of features. As an example, an end user may carry a MSD in conducting themselves throughout the day, such as going for a walk around their neighborhood which may generate a diverse set of sensor recordings. The motion data from the MSD captures fine-grained accelerometer information which can determine the cadence and mode of movement (walking vs. jogging vs. cycling). The image data may capture both the end user and their environment and be analyzed to determine the end user's environmental experience (is it hot, sunny, rainy, cold), as well as the presence of other people and things. GPS sensor data may detect the specific points of travel as well as certain periods of immobility. The motion and bearing data from the MSD indicate that the person is moving from time to time and transiting in specific directions. The audio data provides much context as the end user's interaction. In this example the end user's audio information contains human voice patterns, and the end user can be heard having a conversation with another person. The presence of and analysis of human voices identify that a subject person is discussing topics of the local weather with another person who is in audible proximity. Any photographic images may provide a basis for pattern recognition to identify and classify the specific person the end user interacted with. Many of the features contained within the above narrative exist only in simultaneous analysis of these distinct sensor-driven datasets.

The feature and narrative metadata which is derived from cross-data contextual analysis are much more complete when multiple data sets are brought together to build a corroborating narrative. In this case, in additional to the feature metadata, narrative metadata would be generated by the PRE generated. Such a narrative may describe: "The end user took a 37-minute walk outside, starting and ending at their house. Along the way, they stopped for 6 minutes to have a conversation with Jane, their neighbor who lives 900 m away, about the weather. The end user took 3 pictures which indicate it was a bright, sunny day". The feature 'outside' is itself a hybrid feature made possible only through the analysis of multiple data streams including audio, temperature, location, and movement data. These features becomes searchable at a future point based on this narrative analysis, finding all the end user's interactions with 'Jane', their yearly fitness and mobility habits, the weather patterns of specific times, current events and topics and any other search criteria. Had any of the data elements been absent, it would not have been possible to capture a complete or accurate narrative. Greater or fewer datasets impacts the nature and completeness of the metadata features, narratives, and indices.

Metadata prediction models. In addition to recognizing features directly within the data sets received from an MSD, the PRE also builds models to detect and predict the occurrence of patterns within the metadata that it generates. This analysis allows the PRE to build models which may detect reoccurring patterns which form the basis to a predictable set of events within the data. Predictive models are generated based on frequency and amplitude of classified features within a data subset. Frequency describes the number of times that a feature is recognized within a dataset and may be interpreted through the analysis of metadata. Amplitude refers to the confidence of the classification model in identifying that feature. For example, metadata which describes the gross feature, such as the presence of human speech within a longform audio dataset, may identify key areas where the frequency of speech events is higher. For most people, this will be during their waking hours which will experience numerous peaks and a much higher frequency of occurrence than during their sleeping hours. Therefore, by providing feature metadata as the training data for a predictive neural network, a model is generated which would predict the likelihood of speech throughout certain periods of the day. Such predictions provide a useful means of identifying periods within a dataset where certain features are more likely to occur and monitoring for situations where this prediction is successful or unsuccessful.

Periods of predictive divergence an index of subjective value. The benefits of predictive modelling are realized when reasonably accurate predictive models fail to accurately predict an event. This is called a divergent event. When such divergence events occur, anticipated features either cease to occur or unanticipated features occur. Such divergence events represent periods of heightened change, a specific area of human interest. The degree of divergence may be informed by several characteristics including but not limited to the confidence of the original prediction, the degree of failure (how wrong the prediction was), the frequency of failures, and the number of concurrent failures across multiple predictive models. Examples of such change may include any number of events recorded within an end user's data, such as when they have a new baby, adopt a new hobby, undertake a new activity, relocate for vacation or vocation, or are participating in a new job or role which results in shifts in the frequency of patterns on a temporary or permanent basis. Each of these changes would result in an alternation to predictable patterns within the datasets and would be heightened areas of increased subjective value.

Divergence index forms. By charting the degree of divergence between the recorded events and the predicted events, it is possible to establish a visual representation of these periods of change. As predictive models fail, they form new indices which illustrate 'peaks' of divergence. Divergence 'peaks' represent that the anticipated features within the datasets have changed temporarily, but over time return to their previous patterns. The magnitude of such peaks may be informed on the number of consensus divergences, or simultaneous failures, recognized across multiple datasets. The width of such peaks provide insight into the duration of this divergence. Divergence 'plateaus' might mean the occurrence of features has changed permanently, and that the accuracy of a previously trained model is no longer reliable. In this scenario the model would need to be retrained or a new model generated to factor in the changes in data. The shape and manner of the type of divergence, the degree of consensus across multiple datasets, the duration of divergence, and the magnitude all form insights into the nature of the data and help to describe periods of significant change within longform datasets.

Creation of textual narratives from metadata analysis. The PRE generates categories and metadata outputs which may be used as the basis for establishing textual narratives. The features classified within the datasets may be linked to named categories which may describe the presence of specific entities (which may be translated into nouns) as well as actions (which may be used to define verbs). Nouns are derived by arranging the detected and labeled features within data with verbs which describe the sequences of recognizable events. The PRE references linguistic rules to formulate these lexical fragments into narrative structures to produce sentences which are descriptive and literal narratives of events as they were occurred within the data.

Narrative indices from metadata. Using this method, the PRE evaluates the created metadata and may produce sentences such as "John walks to his front door, picks up his keys. He opens the door, walks through the door. He closes and locks the door". This structure is made possible through the analysis of motion and audio data within the ISD. Motion data detects the action of walking as the end user (John, in this scenario) carries a multimodal sensor. Other sensors detect the change in audio as he moves from room to room in his house, establishing direction. Audio data corroborates the action of picking up keys (the scrape and jangle of the keys), the opening and closing of the door, and the change in acoustic signature of an exterior space versus the previous interior space. Because each of the nouns has been previously classified using categorization models, they can be arranged in a time-based fashion following standard sentence construction to arrange the labeled data into a readable literal narrative. These narratives form lexical indices which support keyword, scenario, and entity-based searching methods as described within the index visualization interface (IVI) in section [400].

400—Index Visualization Interface (IVI)

The index visualization index (IVI) is the primary method of visualizing, interacting with, searching, isolating, and extracting various data subsets collected by this invention.

Taxonomy of classifications. The IVI provides a graphical interface for the review of classified and unclassified collections of features. Classified features may be assigned metadata characteristics to support a comprehensive understanding a person, place, thing, or action described within a data feature. Unclassified features may be visualized by various methods (clusters, hierarchies) and may be assigned named metadata characteristics by the end user. Parameters for the definition of classifications may also be set to create inclusive or exclusive categories of features.

Visualization of indices. The primary function of the IVI is to enable the visualization and interaction of the various indices which have been created within the PRE and utilize these indices to optimize the analysis of sensor-based datasets. The IVI provides numerous graphical user interfaces which allow a user to visualize one or more sensor-based datasets based on the features, narratives, and divergence (predictive failures) of these features. These graphical representations may take many common forms as charts, heatmaps, graphs, tables, or other means of visual representation as the user finds suitable to support various analytical tasks.

Dynamic ranges of datasets and timeframes. Within the IVI, the user may select a dynamic set of datasets recorded from various sources. Specific named datasets based on the sensor designation, type of sensor reading, or format may be selected. Temporally based datasets are commonly displayed along a timeline to correlate their sensor readings. Timelines may be scaled or isolated to select a subset of data samples within specific start and end periods. Datasets may also be selected or limited based on the feature classifications that are contained in the associated metadata.

Search and selection parameters. The IVI facilitates the selection and review of datasets through the searching of indices. Index searching provides a variety of single and concurrent methods including but not limited to searching based on categories of features, frequencies and amplitudes of features, occurrences and magnitudes of novelty within a time period, frequencies and amplitudes of prediction divergence values, the shape of divergences (i.e. 'peaks' verses 'plateaus'), data sources, and narrative or lexical descriptions generated by the PRE. These search methods may be applied individually across all sensor data, temporally defined windows of data, on a sliding timeline against rea-time data.

Feature frequency and novelty visualization. The IVI provides a graphical visualization of the frequencies of features which are identified by the PRE. These frequencies are stored as metadata, which is analyzed by category and characteristic. Metadata from a single dataset may describe single or multiple features, multiple datasets may describe a single feature, and multiple datasets may be used to describe multiple features. Based on the distribution of these features over a timeline, the IVI summarizes and represents the frequency of features. Based on the concurrency of multiple features, feature indices are multiplied to be more prominent. Within an adjustable temporal window, the novelty of features is also graphed, identifying the first occurrence of specific features. Novelty may be binary (only occurring once) or may apply a linear or mathematical falloff formula with each subsequent occurrence incrementally less novel. Compound novelty, concurrent features which are novel within the same variable time unit, also may be multiplied to make such events more prominent.

Lexical noun, verb, and narrative visualization. The IVI provides a graphical representation of lexical information generated by the PRE. As denoted above, the PRE utilizes the categories of features to derive types of words, such as nouns and verbs, to form the basis of textual descriptive narratives. These narratives may be short or long sentence, sentence fragments, or words which provide a means of analyzing and interpreting the features which are contained within a dataset. These lexical passages may be presented in both text format as well as keyword summaries which define in brief the entities and actions recognized through the PRE classification process.

Prediction and divergence visualization. The IVI generates a representation of the magnitude of prediction divergence experienced within a dataset. As predictions may fail across single datasets or multiple datasets concurrently, these visualizations provide a means of identifying areas of minor or major change. Visualized representations incorporate variability in number of datasets, data type, time, and classifications of metadata used within the prediction. The degree of divergence may be indicated in both the magnitude of divergence as well as the rapidity of divergence based on the variable time units (hours, minutes, days, etc.). Areas of heightened divergence provide a visual means of identifying potential datasets for additional investigation.

Isolation and export. The IVI allows for the isolation of data subsets for export. Isolated datasets may be extracted and sent to alternate modules outside of this invention for additional processing. The isolation method provides a means by which the user can also identify additional metadata for a defined period, which is written back to the ISD for storage. Data subsets may be exported in a variety of formats.

Event emission. The IVI provides a mechanism to emit events when the frequency and amplitude of feature or divergence indices meet specific thresholds or when certain lexical keywords or sentences occur. Emitted events may serve as triggers for additional actions to be initiated, such as a call an alternate module outside of the scope of this invention. Emission supports the processing of data in real time where specific emergent patterns would be used to activate one or more external processes.

Data disposition. At the user's discretion, the IVI may provide metadata back to the ISD to support the disposition of data. If the user identifies a specific dataset as being suitable for disposition, either through direct review of the data, the review of indexing of features, divergence, or metadata, or specific numeric criteria, the ISD will receive this disposition request and remove the identified data based on the identified durations, datasets, and features. Disposition may also be applied to the metadata associated to this specific time period.

Benefits for the End User

This invention provides a myriad of benefits for the end user which are unmet within the current state of technology today. These benefits include:

This invention provides a means of identifying information of value from detailed recordings which would otherwise be too lengthy to be processed manually.

This invention provides a unified method to compare diverse types of sensor-based data which otherwise would be difficult to compare due to the structures and characteristics of these datasets.

This invention optimizes the end user's time by allowing them to quickly isolate and extract key events from a historical record.

This invention provides a means of data visualization which provides deeper insights into the contents of sensor data than existing numeric-based methods.

This invention enables the searching of named features within any type of sensor-based data, enabling new forms of patterned-based analysis to identify and extract features from a range of sensor-based datasets.

This invention provides a means of identifying causation and correlation of data features across multiple sensor types and datasets, producing patterns of metadata which may be analyzed to better understand the relationships between data features contained within these disparate datasets.

This invention provides a means of generating indices which may be utilized to extract data subsets for the purpose of supporting the training of neural network-based pattern recognition models.

This invention provides an effective vehicle for transferring knowledge of personal and social interest between generations supporting enculturation, identity, and education with a level of insight and detail unavailable through more limited duration data samples.

This invention provides a means of interacting with indices representing recognizable patterns of human action, movement, speech which is not present in other modes of representation.

This invention will provide the descendants of a human a means of reviewing extensive sensor-based records of lived history, personality, and experiences to derive a comprehensive biographical history.

This invention will support the creation of bodies of knowledge for future historical and anthropological researchers.

This method will preserve intangible cultural artifacts, such as language, oral histories, factual recordings of events, cultural mores and actions, rituals, sayings, and experiences, reducing the risk that the loss of each generation will result in the irretrievable loss of culture or human knowledge and addressing the mandate of large organizations such as the Intangible Cultural Heritage branch of the United Nations Economical, Scientific, and Cultural Organization (UNESCO).

This invention will support the recall of events that the individual was present for or to provide insight into events where the individual has no memory such as when they are sleeping, were absent, or for which they no longer can recall due to natural or artificial memory loss.

This invention will enable the end user to identify information which can be analyzed from longform datasets to make critical observations on individual and social patterns, habits, and natural or biological rhythms, such as those within their own lifetime.

This invention will enhance the speed and accuracy of individual and group recall through the ability to leverage the pattern recognition engine to quickly locate and replay critical information.

This invention will enable the ability to share key insights within the end user's datasets to a social community of peers, family, community, and society.

This invention will enable greater self-reflection of the user on how to optimize the time within their lifespan visualizing trends and patterns represented for any era that their data covers.

This invention will provide a significant optimization in data storage using a pattern recognition engine to enable the identification and disposition of low value data.

The system is set to run on a computing device or mobile electronic device. A computing device or mobile electronic device on which the present invention can run would be comprised of a CPU, Hard Disk Drive, Keyboard, Monitor, CPU Main Memory and a portion of main memory where the system resides and executes. The modules described may be collocated on one computing device or distributed across a number of separate computing devices. Computer and mobile electronic devices like these are well known in the art and are not pertinent to the invention. The system can also be written in a number of different languages and run on a number of different operating systems and platforms and be delivered remotely or as an isolated, stand-alone application located on or off site.

Although the present invention has been described in considerable detail with reference to certain preferred versions thereof, other versions are possible. Therefore, the point and scope of the appended claims should not be limited to the description of the preferred versions contained herein.

As to a further discussion of the manner of usage and operation of the present invention, the same should be apparent from the above description. Accordingly, no further discussion relating to the manner of usage and operation will be provided.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Thus, it is appreciated that the optimum dimensional relationships for the parts of the invention, to include variation in size, materials, shape, form, function, and manner of operation, assembly and use, are deemed readily apparent and obvious to one of ordinary skill in the art, and all equivalent relationships to those illustrated in the drawings and described in the above description are intended to be encompassed by the present invention.

Furthermore, other areas of art may benefit from this method and adjustments to the design are anticipated. Thus, the scope of the invention should be determined by the appended claims and their legal equivalents, rather than by the examples given.

The embodiments of the invention in which an exclusive property or privilege is claimed are defined as follows:

1. A system for indexing and analyzing extended biographical human data, comprising:
   one or more processor and memory;
   a multimodal sensor device (MSD) array configured to capture a comprehensive range of data including physiological, environmental, and social interaction information pertinent to an individual's daily experiences and continuously monitor and record biographical data reflecting an individual's physiological states, environmental contexts, and social interactions over extended periods, facilitating the construction of a comprehensive and dynamic biographical profile that captures both conscious and unconscious aspects of the individual's lived history, personality, and experiences to derive a comprehensive biographical history;
   an information storage device (ISD) that is either a physical unit or a virtual construct connected via a local private network or a communication network, purposed for the storage and longitudinal management of biographical data across extensive timescales;
   a pattern recognition engine (PRE) that operationalizes core functions by transforming the collected raw biographical data within the ISD into structured metadata through the application of specialized algorithms and machine learning methods, such as artificial neural networks, which are expressly designed for the detection, classification, and projection of human behavioral patterns, wherein the pattern recognition engine (PRE) constructs classification and predictive models for specific time-based segments of data, essential for capturing the dynamic nature of human biographical information;
   the PRE assesses model performance metrics, such as accuracy and confidence, to pinpoint periods indicative of significant changes in data patterns, serving as markers for the novelty and variability within an individual's life events;
   the system generates metadata indices that chronicle the occurrence and context of model performance shifts, including the enumeration of simultaneous discrepancies across various models and datasets, as well as the temporal and proximity of these events; and
   such metadata indices delineate both transient and enduring shifts in data patterns, enabling a thorough understanding of the individual's behavioral changes over time; and
   an index visualization index (IVI) serving as the primary system for visualization, user interaction, and manipulation of the collected data subsets, wherein the IVI is responsible for the generation of narrative constructs and predictive behavioral models that enable users to reflect upon and comprehend their biographical patterns, thus supporting immediate behavioral modifications informed by the synthesis of historical and contemporaneous data analysis.

2. The system of claim 1, wherein the multimodal sensor device (MSD) array includes
   a digital hardware configuration featuring one or more microprocessors specifically optimized for the capture and digitization of sensory data relevant to human biographical information; and
   wherein each MSD in the array integrates a selection of sensors or peripheral devices, purpose-built to collect detailed environmental and physiological data that reflects the nuances of an individual's daily experiences, subsequently converting this information into digital formats for in-depth analysis by the pattern recognition engine (PRE).

3. The system of claim 1, wherein the information storage device (ISD)
   is configured as a dedicated repository for systematically receiving, securely storing, and efficiently retrieving sensor data pertinent to human biographical information, as captured by the multimodal sensor device (MSD) array;
   the ISD includes a tailored assembly of hardware components comprising at least one microprocessor, data transmission modules for both wired and wireless communication, volatile memory for rapid data access, and long-term data storage solutions; and
   the ISD is further configured with a selection of software optimized for biographical data management, including a robust operating system, a scalable database architecture, specialized web server software, and a messaging queue system to facilitate data processing and user interaction.

4. The system of claim 1, wherein
   the information storage device (ISD) employs specialized database software applications designed to capture and structure sensor data into diverse, searchable formats tailored for biographical analysis; the ISD systematically generates indices for the datasets, and
   wherein each index serves as a synthesized summary of key data points, enhancing the efficiency and accuracy of data search and retrieval processes related to the individual's biographical history.

5. The system of claim 1, wherein the pattern recognition engine (PRE)
   is configured to generate metadata that precisely identifies and categorizes features, patterns, and predictive behaviors within the sensor data, utilizing tailored neural network models and algorithmic parameters specifically developed for biographical data analysis;
   the PRE stores these models within the ISD, where they can be systematically accessed, operated, and refined based on ongoing analysis; the metadata, structured as data objects, is intricately linked to corresponding datasets within the ISD and includes critical time-stamped information to correlate each classification with its source data; such metadata includes but is not limited to human-readable text labels and quantifiable confidence scores for each label; and the PRE is designed to handle and analyze a broad spectrum of data types, including but not limited to audio, motion, sensor, and time-series data, and is adept at processing and interpreting a diverse array of data types and formats stored within the ISD to support the construction of a detailed biographical narrative.

6. The system of claim 1, wherein the metadata generated by the pattern recognition engine (PRE) establishes a foundational framework for the categorization, indexing, and interactive querying of biographical data within the information storage device (ISD);

the PRE the PRE executes a sequence of data processing operations tailored to the nuanced analysis of human biographical data;

the PRE develops and maintains an evolving collection of neural network models that are specifically trained and periodically refined using diverse and longitudinal data captured by the ISD; and models are derived from an analysis that integrates both singular and multiple data sources, and the training regimen for these models is adapted to include variable time ranges, ensuring comprehensive coverage of the individual's biographical timeline.

7. The system of claim 1, wherein the pattern recognition engine (PRE) generates metadata indices that quantify the frequency of feature occurrences within specific datasets over designated time periods, reflecting the rhythmic patterns of an individual's activities; and the PRE further creates metadata indices that highlight the novelty of features, capturing the emergence of new behaviors or events within the datasets; the system computes metadata index values that not only measure the frequency of recurring features but also the emergence of novel features across multiple datasets, providing a multi-layered view of an individual's evolving biographical landscape over time.

8. The system of claim 1, wherein the pattern recognition engine (PRE) utilizes a combination of advanced evaluation methods within the information storage device (ISD) to detect gross features, characterized by the onset, duration, and cessation of distinct periods within the sensor data that exhibit significant amplitude or frequency variations;

the system employs variable duration data sampling (VDDS) techniques to discern fine features, pinpointing precise characteristics within targeted subsets of the sensor data; and the PRE integrates both static, rule-based algorithms and dynamically trained neural network models to conduct comprehensive feature recognition, thereby enabling the nuanced analysis of sensor data that contributes to the detailed profiling of an individual's biographical information.

9. The system of claim 1, wherein the pattern recognition engine (PRE) implements specialized neural networks to manage high variability in sensor data;

this includes the deployment of both supervised and unsupervised learning neural networks for robust feature classification;

specifically, the PRE employs unsupervised neural networks to discern and cluster emergent features within the sensor data, features for which prior training data may not exist; and these neural networks organize features into clusters based on inherent similarities rather than pre-established categories, forming cluster groups that reflect the relational proximity of data points to a conceptual centroid within the feature space, and enabling the dynamic categorization of biographical data elements based on their interrelationships.

10. The system of claim 1, wherein the pattern recognition engine (PRE) is configured to extract and analyze multiple features within the same dataset by applying an array of refined algorithms and specifically trained neural network models;

the PRE processes distinct samples of sensor data across varying durations, as determined by the variable duration data sampling (VDDS), to categorize a comprehensive set of gross features within the dataset, pinpointing their precise occurrences and contributing to the enrichment of metadata storage; and following the identification of gross features, the PRE conducts fine feature analysis to delineate and classify these features into more granular and specific metadata elements, which are then utilized to create and refine metadata indices that encapsulate the individual's biographical information with enhanced accuracy and detail.

11. The system of claim 1, wherein the pattern recognition engine (PRE) utilizes data filters tailored to specific data types within the sensor data spectrum, including but not limited to audio, visual, motion, and environmental data; and these filters are strategically applied to both raw sensor data and the resulting metadata, with the filtering criteria being defined by algorithms with precise mathematical or numerical parameters, as well as by neural network models that have been trained to selectively identify, extract, or omit data points based on their relevance to constructing an individual's biographical profile.

12. The system of claim 1, wherein the pattern recognition engine (PRE) is configured to perform re-analysis of previously processed sensor data following the enhancement or updating of its neural network models or the refinement of its algorithmic parameters; and this re-analysis is conducted to leverage improvements in the models or algorithms, resulting in incremental advancements in the precision and accuracy of feature identification within the biographical datasets, thereby ensuring that the evolving narrative of an individual's life is captured with the utmost fidelity.

13. The system of claim 1, wherein the pattern recognition engine (PRE) incorporates advanced data-specific synthesis methods tailored to enhance feature recognition across various sensor data types;

the system utilizes additive data synthesis techniques to create enriched training datasets for time-series sensors, facilitating the development of a detailed metadata set that accurately delineates the location, attributes, and characteristics of each identified feature;

the PRE performs cross-data contextual analysis to detect and interpret concurrent or related features across multiple datasets, enabling the creation of metadata indices that reflect the interconnectedness of events and behaviors within an individual's biographical data; the system's predictive models, constructed by the PRE, are adept at identifying and forecasting emergent patterns within the metadata, with the creation of divergence indices that measure the variances between actual occurrences and anticipated events; and the PRE is designed to generate textual narratives from the metadata, translating the structured metadata into coherent narratives that offer a descriptive account of the individual's life experiences, with the narrative indices serving as a basis for searchable and analyzable content within the system.

14. The system of claim 1, wherein the index visualization index (IVI)

offers an advanced graphical user interface that facilitates the examination and categorization of both classified and unclassified feature sets within the datasets;

the IVI assigns detailed metadata characteristics to classified features, enhancing the visualization and interpretability of data related to specific aspects of an individual's biographical history;

this interface supports refined search functionalities, enabling both broad and narrow queries within the datasets; and the IVI provides visualization techniques for unclassified features, allowing end users to interactively assign descriptive metadata characteristics, thereby contributing to the continuous refinement and accuracy of the biographical data repository.

15. The system of claim 1, wherein datasets the index visualization interface (IVI) is equipped to display and facilitate interaction with the array of indices generated by the pattern recognition engine (PRE), leveraging these indices to enhance the analysis and understanding of sensor-based biographical datasets;

the IVI presents a suite of graphical user interfaces that enable users to visualize sensor-based datasets in relation to identified features, narrative constructs, and divergence indicators such as classification discrepancies or predictive model anomalies; and the IVI's graphical representations, which include but are not limited to charts, heatmaps, graphs, and tables, are customizable to user preferences and analytical requirements, thereby supporting a diverse range of analytical tasks and personal insights into an individual's life history.

16. The system of claim 1, wherein index visualization interface (IVI) facilitates the selection and dynamic integration of datasets recorded from a multitude of sensor sources, enabling the targeted selection of datasets identified by specific sensor designations, types of sensor readings, or data formats;

the IVI features an interactive timeline display that aligns temporally based datasets to visually correlate sensor readings across time, with functionality for scaling or isolating the timeline to focus on data subsets within precise temporal boundaries; and the IVI allows for the selection and filtering of datasets grounded in the feature classifications derived from the structured metadata, ensuring a user-centric approach to data interaction that aligns with the narrative context of the individual's biographical data.

17. The system of claim 1, wherein the index visualization interface (IVI) incorporates advanced graphical tools to visualize the frequency of features as identified by the pattern recognition engine (PRE), with such feature frequencies cataloged as metadata;

this metadata is methodically analyzed and categorized, capturing both singular and aggregate feature occurrences across individual and collective datasets;

the IVI employs temporal visualization techniques to summarize and represent feature frequencies, illustrating the distribution and interplay of features over time; and furthermore, the IVI amplifies feature indices in instances of concurrent feature occurrences across datasets, enhancing the visibility and significance of correlated events within the individual's biographical narrative.

18. The system of claim 1, wherein the index visualization interface (IVI) graphically represents the novelty of features within an adjustable temporal window, pinpointing the initial emergence of specific features within the sensor data;

the system delineates novelty as either binary for unique occurrences or applies a quantitative falloff formula to rate the diminishing novelty of recurring features; and additionally, the IVI highlights compound novelty by accentuating the significance of simultaneous novel features that arise within the same temporal segment, thereby underscoring pivotal moments in the individual's biographical timeline.

* * * * *